US012746226B2

(12) United States Patent
Hsu et al.

(10) Patent No.: US 12,746,226 B2
(45) Date of Patent: Sep. 29, 2026

(54) PHARMACEUTICAL KITS AND USES THEREOF FOR TREATING COLORECTAL CANCER

(71) Applicant: Anbogen Therapeutics, Inc., Taipei City (TW)

(72) Inventors: Tsu-An Hsu, Taipei City (TW); Sue-Ming Chang, Taipei City (TW); Chien-Ting Lin, Taipei City (TW); Meng-Chieh Lin, Taipei City (TW)

(73) Assignee: Anbogen Therapeutics, Inc., Taipei City (TW)

( * ) Notice: Subject to any disclaimer, the term of this patent is extended or adjusted under 35 U.S.C. 154(b) by 337 days.

(21) Appl. No.: 18/430,703

(22) Filed: Feb. 2, 2024

(65) Prior Publication Data

US 2024/0277663 A1 Aug. 22, 2024

Related U.S. Application Data

(60) Provisional application No. 63/444,242, filed on Feb. 9, 2023.

(51) Int. Cl.

| | |
|---|---|
| ***A61K 31/4045*** | (2006.01) |
| ***A61K 39/00*** | (2006.01) |
| ***A61P 35/00*** | (2006.01) |
| ***C07K 16/28*** | (2006.01) |

(52) U.S. Cl.

CPC .......... *A61K 31/4045* (2013.01); *A61P 35/00* (2018.01); *C07K 16/2827* (2013.01); *A61K 2039/505* (2013.01); *A61K 2039/545* (2013.01)

(58) Field of Classification Search

None

See application file for complete search history.

(56) References Cited

FOREIGN PATENT DOCUMENTS

WO WO-2017074317 A1 * 5/2017 .............. A61P 11/00

OTHER PUBLICATIONS

Kanth. British Medical Journal, 2021, 374: n1855, 1-15 (Year: 2021).*

* cited by examiner

*Primary Examiner* — Noble E Jarrell

(74) *Attorney, Agent, or Firm* — NZ Carr Law Office

(57) ABSTRACT

This disclosure in general describes a pharmaceutical kit for treating colorectal cancer; the pharmaceutical kit comprises (E)-N-hydroxy-3-(1-(phenylsulfonyl)-indolin-5-yl)-acrylamide, and an anti-PD-1 or anti-PD-L1 antibody. Furthermore, this disclosure describes a method for treating colorectal cancer in a subject, comprising administering to the subject the aforementioned pharmaceutical kit, wherein the (E)-N-hydroxy-3-(1-(phenylsulfonyl)-indolin-5-yl)-acrylamide is given to the subject in a dosage ranging from about 10 μg/kg to 1 g/kg; and the anti-PD-1 or anti-PD-L1 antibody is administered to the subject at a dosage ranging from about 1 μg/kg to 100 mg/kg.

11 Claims, 28 Drawing Sheets

Specification includes a Sequence Listing.

PHARMACEUTICAL KITS AND USES THEREOF FOR TREATING COLORECTAL CANCER

CROSS-REFERENCE OF RELATED APPLICATION

This application claims priority to US. Application No. 63/444,242, filed on Feb. 8, 2023. The content of which application is incorporated herein by reference in its entirety.

SEQUENCE LISTING XML

The present application is being filed along with a Sequence Listing XML in electronic format. The Sequence Listing XML is provided as an XML file entitled "MYHP_0212US_Sequence_Listing.xml," created Jan. 19, 2024, which is 4 Kb in size. The information in the electronic format of the Sequence Listing XML is incorporated herein by reference in its entirety.

BACKGROUND OF THE INVENTION

1. Field of the Invention

The present disclosure in general relates to the field of cancer treatment. More particularly, the present disclosure pertains to a pharmaceutical kit comprising (E)-N-hydroxy-3-(1-(phenylsulfonyl)-indolin-5-yl)-acrylamide (ABT-301) in combination with an anti-PD-1 or anti-PD-L1 antibody for the treatment of colorectal cancer.

2. Description of Related Art

Colorectal cancer is a neoplastic condition localized within the colon or rectum, both constituting integral components of the large intestine. Colorectal cancer has a gradual pathological progression that may span across several years, commonly originating as benign polyps on the mucosal lining of the colon or rectum. Over time, these polyps may transform into cancerous cells, leading to colorectal cancer. There are various types of colorectal cancer, with adenocarcinomas accounting for the majority of colorectal cancer cases. According to the statistics of World Health Organization (WHO), colorectal cancer ranks as the second-leading cause of cancer-related fatalities globally. In 2020, more than 1.9 million new cases of colorectal cancer and more than 930,000 deaths due to colorectal cancer were estimated to have occurred globally. The incidence rates were highest in Europe and Australia and New Zealand, and the mortality rates were highest in Eastern Europe. It was estimated that by 2040 the burden of colorectal cancer will increase to 3.2 million new cases per year (an increase of 63%) and 1.6 million deaths per year (an increase of 73%). Such severe cancer results in significant health and economic burdens on society.

For medical intervention, contemporary approaches to treating colorectal cancer commonly encompass a multifaceted strategy combining surgery, radiotherapy, chemotherapy, and, in certain cases, targeted therapy, and immunotherapy. There are different strategies employed for the management of diseases in their early and advanced stages. For early stage disease (i.e. tumor limited to the bowel or local lymph nodes, with no metastatic dissemination to distant organs), surgical removal of the tumor and nearby lymph nodes is employed. In some cases, a temporary or permanent colostomy or ileostomy may be needed to create an opening for waste elimination. In early-stage colorectal cancer, adjuvant chemotherapy may be recommended to kill any remaining cancer cells that cannot be seen or removed during surgery, or may be given before surgery (neoadjuvant chemotherapy) to shrink the tumor. Radiation therapy can be applied for tumors of rectum to reduce the size of the tumor. For advanced stage disease, systemic therapy, such as chemotherapy, is the primary treatment approach for metastatic colorectal cancer. Targeted therapy may be used in combination with chemotherapy for patients with specific genetic mutations, such as KRAS or BRAF mutations. Immunotherapy drugs may be considered for patients with tumors that exhibit specific genetic markers, such as microsatellite instability-high (MSI-H) or mismatch repair deficiency (dMMR).

While advancements in medical interventions have enhanced prognosis for many patients, there are limitations to current therapies. For example, surgical intervention is an invasive therapeutic measure that results in direct harm to patients; the administration of temporary or permanent colostomy or ileostomy significantly impacts the patient's quality of life. Chemotherapy may yield significant side effects, such as nausea and vomiting, loss of appetite, fatigue, oral sores and ulcers, and alopecia. Further, the efficacy of chemotherapy varies among individual patients, and the emergence of resistance to chemotherapy over time poses additional challenges for the long-term management of tumors.

In view of the foregoing, there exists in the related art a need for improved therapeutics in the treatment of colorectal cancer, with the aim of augmenting therapeutic efficacy, mitigating adverse effects, and safeguarding the quality of life for patients.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

Pursuant to the foregoing, the primary objective of the present disclosure is to furnish an improved therapeutic modality for the treatment of colorectal cancer. As embodied and broadly described herein, one aspect of the disclosure is directed to a pharmaceutical kit for treating colorectal cancer in a subject; the pharmaceutical kit comprises

- a first container containing (E)-N-hydroxy-3-(1-(phenylsulfonyl)-indolin-5-yl)-acrylamide; and
- a second container containing an anti-PD-1 or anti-PD-L1 antibody.

According to some embodiments of the present disclosure, the anti-PD-1 antibody is selected from the group consisting of cemiplimab, pembrolizumab, nivolumab, and RMP1-14. Also, the anti-PD-L1 antibody is selected from the group consisting of atezolizumab, avelumab, and durvalumab.

Preferably, the colorectal cancer treatable with the present pharmaceutical kit is a microsatellite stable-type or microsatellite instable-type colorectal cancer. Further, the colorectal cancer may be an in situ colorectal cancer or a metastatic colorectal cancer.

Another aspect of the present disclosure pertains to a method for the treatment of colorectal cancer in a subject with the aid of using the present pharmaceutical kit, comprising administering to the subject the present pharmaceutical kit, wherein the (E)-N-hydroxy-3-(1-(phenylsulfonyl)-indolin-5-yl)-acrylamide is administered to the subject in the amount of about 10 μg/kg-1 g/kg; and the anti-PD-1 or anti-PD-L1 antibody is administered to the subject in the amount of about 1 μg/kg-100 mg/kg.

More preferably, the (E)-N-hydroxy-3-(1-(phenylsulfonyl)-indolin-5-yl)-acrylamide is administered to the subject in the amount of about 2.5-10 mg/kg; and the anti-PD-1 or anti-PD-L1 antibody is administered to the subject in the amount of about 100 μg/kg-1 mg/kg.

Examples of the anti-PD-1 antibody used in the present pharmaceutical kit may be cemiplimab, pembrolizumab, nivolumab, or RMP1-14. Alternatively, the anti-PD-L1 antibody suitable for use in the present pharmaceutical kit may be atezolizumab, avelumab, and durvalumab.

In the preferred embodiments, the colorectal cancer treatable with the present pharmaceutical kit is a microsatellite stable-type or microsatellite instable-type colorectal cancer. Further, the colorectal cancer may be an in situ colorectal cancer or a metastatic colorectal cancer.

The subject treatable by the present pharmaceutical kit or the present method is a mammal, for example, a human, a mouse, a rat, a guinea pig, a hamster, a monkey, a swine, a dog, a cat, a horse, a sheep, a goat, a cow, and a rabbit. Preferably, the subject is a human.

Subject matters that are also included in other aspects of the present disclosure include a pharmaceutical composition that includes a pharmaceutical combination described herein and a pharmaceutically acceptable excipient, and use of a pharmaceutical kit or a pharmaceutical composition in the manufacture of a medicament for treating a colorectal cancer in a subject in need thereof.

Many of the attendant features and advantages of the present disclosure will becomes better understood with reference to the following detailed description considered in connection with the accompanying drawings.

BRIEF DESCRIPTION OF THE DRAWINGS

These and other features, aspects and advantages of the present invention will become better understood with reference to the following description, appended claims and the accompanying drawings, where:

FIGS. 1E-1F depict the tumor volume over 28 days (FIG. 1E) and on Day 28 (FIG. 1F); and FIG. 1G illustrates the survival rate of the mice after the indicated treatments;

FIGS. 2I-2J depict the tumor volume over 24 days (FIG. 2I) and on Day 21 (FIG. 2J) in the mice after the indicated treatments;

FIGS. 3I-3J depict the tumor volume over 27 days (FIG. 3I) and on Day 17 (FIG. 3J) in the mice after the indicated treatments;

FIGS. 4G-4H depict the tumor volume over 25 days (FIG. 4G) and on Day 25 (FIG. 4H), with the exception of the vehicle group, which displays results up to Day 20 due to reaching the humane endpoints; and FIG. 4I illustrates the survival rate of the mice after the indicated treatments; FIGS. 5I-5K depict the tumor volume over 49 days (FIG. 5I) and on Day 22 (FIG. 5J) and on Day 31 (FIG. 5K, wherein the indicated treatments were discontinued) in the mice after the indicated treatments.

DESCRIPTION

Figure 1A:
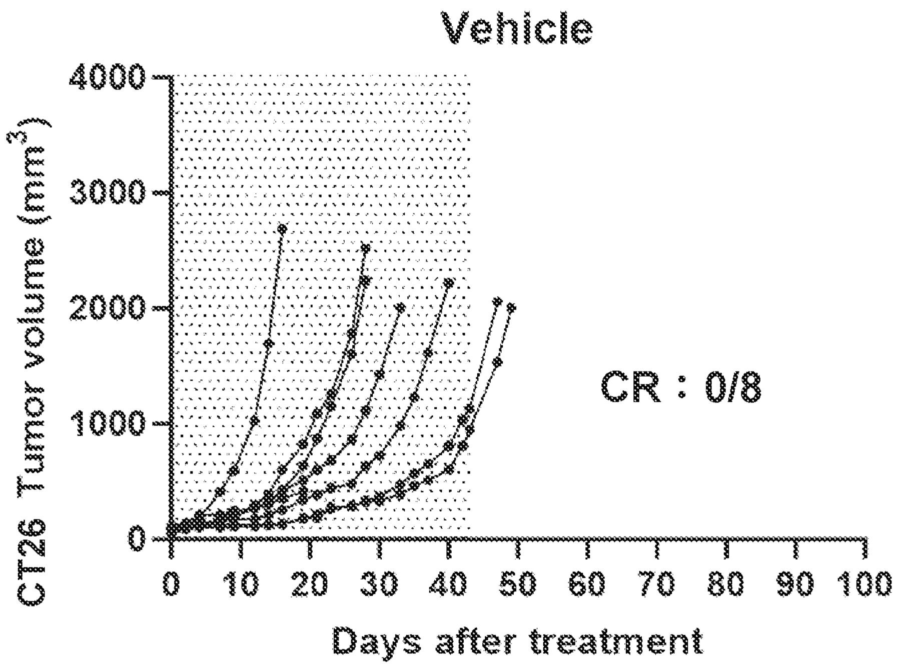
FIGS. 1A-1G are the results of treating mice bearing CT26 (a microsatellite stable (MSS) subtype colorectal carcinoma cell line) with a combination of ABT-301 and avelumab (an anti-PD-L1 antibody), in which FIGS. 1A-1D respectively illustrate the number of mice exhibiting a complete response (CR) in the indicated treatment groups (n=8/group)
Figure 1B:
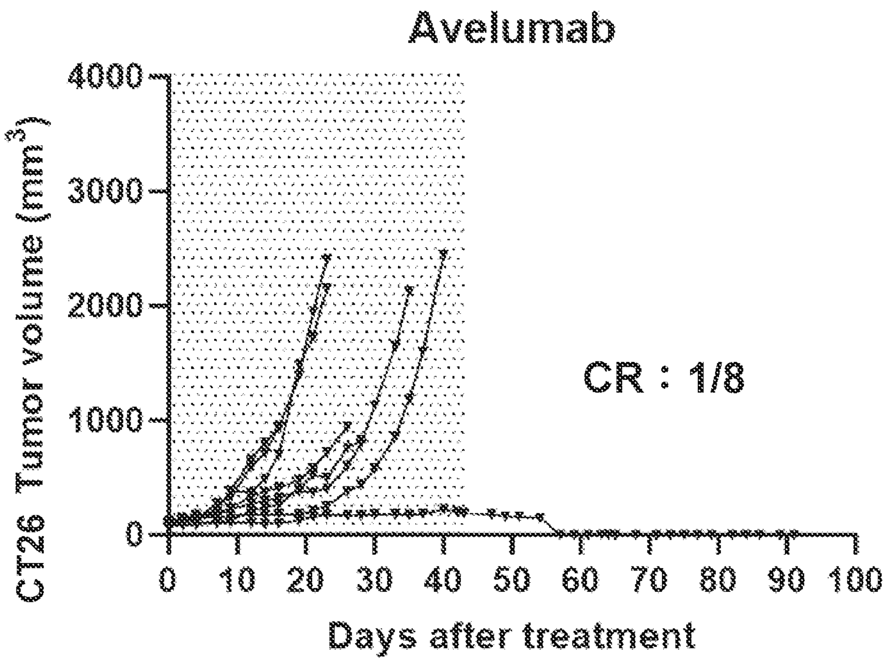
Figure 1C:
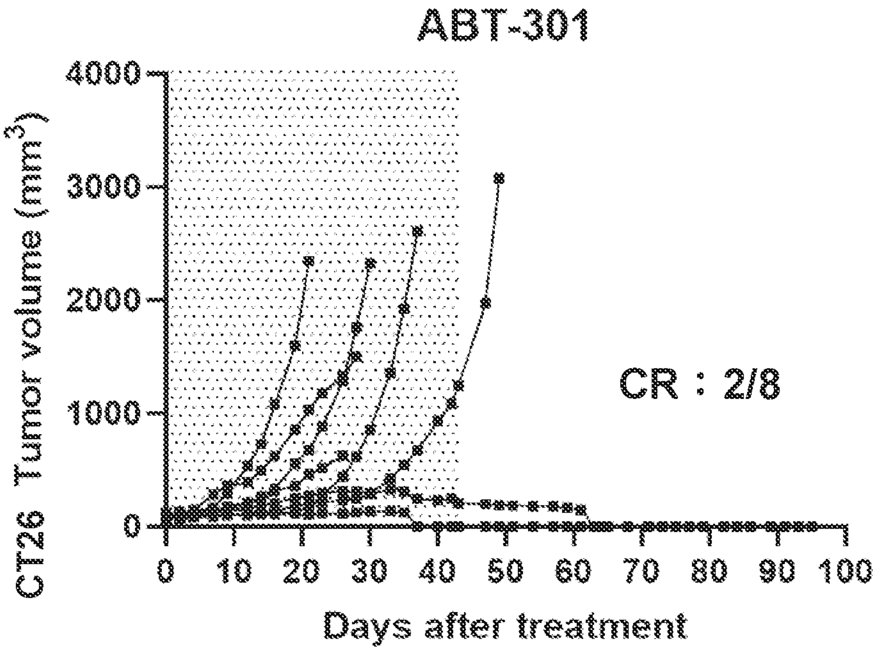
Figure 1D:
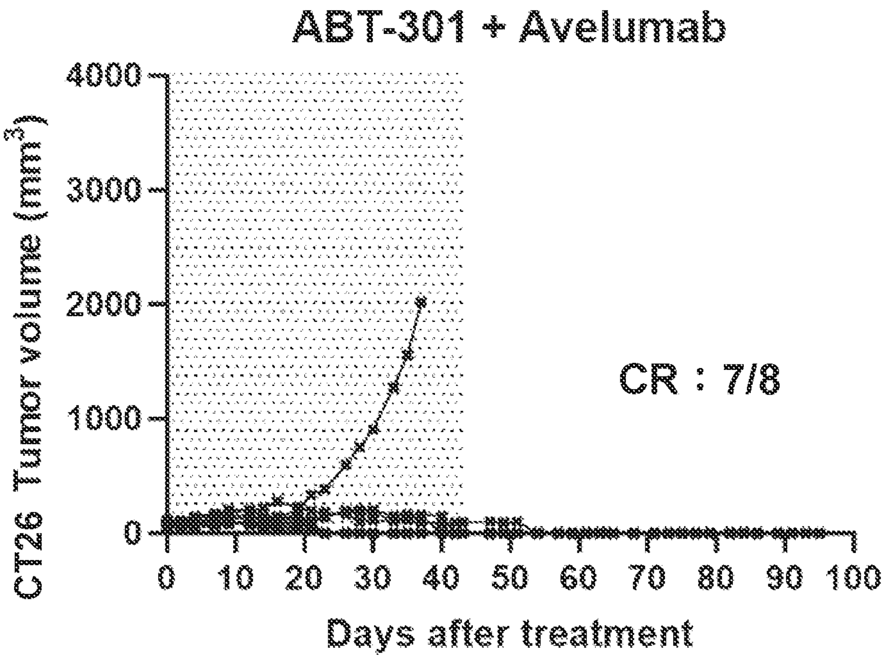

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a," "an," and "the" include the plural reference unless the context clearly dictates otherwise. Also, as used herein and in the claims, the terms "at least one" and "one or more" have the same meaning and include one, two, three, or more. The practice of the present invention will employ, unless otherwise indicated, conventional techniques of molecular biology, microbiology, recombinant DNA, and immunology, which are within the skill of the art. Such techniques are explained fully in the literature.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Colorectal cancer may be classified according to the traditional histological subtypes as defined by WHO. The most common subtype is adenocarcinoma not otherwise specified, which accounts for 85% of colorectal cancer cases worldwide. The second most common subtype is mucinous carcinoma, characterized by the presence of mucinous lakes in at least 50% of the tumor area, which accounts for 5-20% of colorectal cancer cases worldwide. Medullary carcinoma, characterized by solid growth in combination with an inflammatory reaction, has been estimated to be 4%. Signet-ring cell carcinoma accounts for less than 2% of colorectal cancer cases worldwide. Alternatively, colorectal cancer may be classified in accordance with molecular classifications, in which (1) DNA mismatch repair-proficient/microsatellite stable (pMMR/MSS) or (2) DNA mismatch repair-deficient and microsatellite instable-high (dMMR/MSI-H) is a key criterion for the classification of colorectal cancer. Colorectal cancer of the MSI-H (or dMMR/MSI-H) subtype accounts for only 8-10% of all colorectal cancer cases, and 90% of colorectal cancer patients are pMMR/MSS. Microsatellite instability (MSI) and conversably microsatellite stability (MSS) may be determined by a pentaplex PCR, using the mononucleotide MSI markers BAT-25, BAT-26, NR-21, NR-22 and NR-24; MSI is defined positive when three or more of the foregoing five markers showed allelic size variants.

The terms "treatment" and "treating" as used herein may refer to a curative or palliative measure. The term "treating" encompasses partially or completely preventing, ameliorating, mitigating, and/or managing a symptom, a secondary disorder, or a condition associated with colorectal cancer. The term "treating" as used herein refers to application or administration of the present pharmaceutical kit and/or method to a subject, who has a symptom, a secondary disorder, or a condition associated with colorectal cancer, with the purpose to partially or completely alleviate, ameliorate, relieve, delay onset of, inhibit progression of, reduce severity of, and/or reduce incidence of one or more symptoms, secondary disorders, or features associated with colorectal cancer. Symptoms, secondary disorders, and/or conditions associated with colorectal cancer include, but are not limited to, fever, weakness, fatigue, weight loss, pain, cough, bleeding, skin change, diarrhea or constipation, nausea, vomiting, and loss of appetite. Treatment may be administered to a subject who exhibits only early signs of such symptoms, disorders, and/or conditions for the purpose of decreasing the risk of developing the symptoms, secondary disorders, and/or conditions associated with colorectal cancer. Treatment is generally "effective" if one or more symptoms or clinical manifestations or markers are reduced as that term is defined herein. Alternatively, a treatment is "effective" if the progression of a symptom, disorder, or condition is reduced or halted.

The term "administered," "administering" or "administration" are used interchangeably herein to refer either directly administering the pharmaceutical kit of the present disclosure, which comprises the (E)-N-hydroxy-3-(1-(phenylsulfonyl)-indolin-5-yl)-acrylamide and the anti-PD-1 or anti-PD-L1 antibody.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms, or as milligrams per kilogram of body weight (mg/kg). Alternatively, the effective amount can be expressed in the concentration of the active component (e.g., the present agent ABT-301), such as molar concentration, mass concentration, volume concentration, molality, mole fraction, mass fraction and mixing ratio. Specifically, the term "therapeutically effective amount" used in connection with the agent described herein refers to the quantity of the agent, which is sufficient to alleviate or ameliorate the symptoms associated with the colorectal cancer in the subject. Persons having ordinary skills could calculate the human equivalent dose (HED) for the medicament (such as the present agent ABT-301) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" or "patient" refers to an animal including the human species that is treatable with the pharmaceutical kit and/or method of the present disclosure. The term "subject" or "patient" intended to refer to both the male and female gender unless one gender is specifically indicated. Accordingly, the term "subject" or "patient" comprises any mammal which may benefit from treatment of colorectal cancer. Examples of a "subject" or "patient" include, but are not limited to, a human, a rat, a mouse, a guinea pig, a monkey, a pig, a goat, a cow, a horse, a dog, a cat, a bird, and a fowl. In an exemplary embodiment, the subject is a human.

As described herein, tumor responses were evaluated using Response Evaluation Criteria in Solid Tumors (RECIST) criteria. Complete response (CR) was defined as complete disappearance of measurable or evaluable tumor lesions; partial response (PR) was defined as reduction of the size of measurable tumor lesions by at least 30% (≥30%) compared to the original tumor size; stable disease (SD) was defined as reduction of the size of measurable tumor lesions by less than 30% (<30%) or enlargement of the size of measurable tumor lesions by less than 20% (<20%) compared to the original tumor size; and progressive disease (PD) was defined as growth of the tumor by more than 30%

(>30%) in the tumor volume compared to the original tumor size or development of new lesions.

II. Description of the Invention

The present disclosure is, at least in part, based on the discovery that the compound (E)-N-hydroxy-3-(1-(phenylsulfonyl)-indolin-5-yl)-acrylamide (ABT-301) manifests efficacy against colorectal cancer. Further, it is noteworthy that ABT-301 enhances the effect of immunotherapy for the treatment of colorectal cancer, not limited to the MSI-H subtype but also, notably, to the challenging refractory MSS subtype of colorectal cancer. In accordance with the foregoing, ABT-301 demonstrates a synergistic effect in the treatment of colorectal cancer when administered in conjunction with immunotherapy, particularly with an immune checkpoint inhibitor, such as an anti-PD-1, an anti-PD-L1 antibody, and the like.

1. The Pharmaceutical Kit

Accordingly, the first aspect of the present disclosure pertains to a pharmaceutical kit for treating colorectal cancer in a subject in need thereof. According to embodiments of the present disclosure, the present pharmaceutical kit comprises:

- a first container containing (E)-N-hydroxy-3-(1-(phenylsulfonyl)-indolin-5-yl)-acrylamide; and
- a second container containing an anti-PD-1 or anti-PD-L1 antibody.

In essence, the present agent ABT-301 demonstrates a preferential inhibitory capacity towards classes I and IIb histone deactylase (HDAC), including HDAC1, HDAC2, and HDAC3 that are respectively class I HDAC, and HDAC6 and HDAC10 that belong to class IIb HDAC. In the treatment of colorectal cancer, ABT-301 not only confers tumor cell apoptosis, but also the enhanced therapeutic effect of immunotherapy, particularly with regard to the refractory MSS subtype of colorectal cancer.

In general, anti-PD-1 antibody suitable for use in the present pharmaceutical kit may be cemiplimab, pembrolizumab, nivolumab, or RMP1-14; preferably, anti-PD-1 antibody suitable for use in the present pharmaceutical kit is RMP1-14. Alternatively, the present pharmaceutical kit may include an anti-PD-L1 antibody, which may be any one of atezolizumab, avelumab, or durvalumab; preferably, the anti-PD-L1 antibody suitable for use in the present pharmaceutical kit is avelumab.

Without being bound by the theory, other options for immune checkpoint inhibitors may be utilized in the present pharmaceutical kit; such immune checkpoint inhibitor options may be an anti-CTLA4 antibody, such as ipilimumab, tremelimumab, zalifrelimab, and the like.

Optionally or additionally, other agent for immunotherapy may be included within the present pharmaceutical kit. Said immunotherapeutic agent may be selected from the group consisting of C—C motif chemokine ligand 3 (CCL3), C—C motif chemokine ligand 26 (CCL26), C—X—C motif chemokine ligand 7 (CXCL7); granulocyte colony-stimulating factor (G-CSF), granulocyte macrophage colony-stimulating factor (GM-CSF), interferon-α (IFN-α), interferon-β (IFN-β), interferon-γ (IFN-γ), tumor necrosis factor-α (TNF-α); interleukin-4 (IL-4), interleukin-5 (IL-5), interleukin-7 (IL-7), interleukin-10 (IL-10), interleukin-12 (IL-12), interleukin-13 (IL-13), interleukin-15 (IL-15); apremilast, imiquimod, lenalidomide, pomalidomide, sipuleucel-T, thalidomide; anti-CD2 antibody, anti-CD3 antibody, anti-CD4 antibody, anti-CD11a antibody, anti-CD20 antibody, anti-CD25 antibody, anti-CD52 antibody, anti-EGFR antibody, anti-HER2 antibody, anti-PCDP1 antibody, anti-SLAMF7 antibody, and anti-Trop-2 antibody.

For the purpose of treating colorectal cancer, the present pharmaceutical kit may additionally include a chemotherapeutic agent or a targeted therapeutic agent. Illustrative chemotherapeutic agent includes, but is not limited to, actinomycin D, aminoglutethimide, amsacrin, anastrozol, anthracycline, bexaroten, bleomycin, buselerin, busulfan, camptothecin derivates, capecitabin, carboplatin, carmustine, chlorambucil, cisplatin, cladribin, cyclophosphamide, cytarabin, cytosinarabinoside, dacarbacin, dactinomycin, daunorubicin, docetaxel, doxorubicin, epirubicin, estramustine, etoposid, exemestan, fludarabin, fluorouracil, formestan, gemcitabin, goselerin, hycamtin, idarubicin, ifosfamid, imatinib, irinotecan, letrozol, leuprorelin, lomustin, melphalan, mercaptopurine, methotrexate, miltefosin, mitomycine, mitoxantron, nimustine, oxaliplatin, paclitaxel, pentostatin, procarbacin, temozolomid, teniposid, testolacton, thiotepa, thioguanine, topotecan, treosulfan, tretinoin, triptorelin, trofosfamide, vinblastine, vincristine, vindesine, and vinorelbine.

According to the embodiments of the present disclosure, said targeted therapeutic agent may be bortezomib, dasatinib, erlotinib, gefitinib, lapatinib, nilotinib, sorafenib, sunitinib, tofacitinib, crizotinib, venetoclax, obatoclax, navitoclax, gossypol, olaparib, rucaparib, niraparib, talazoparib, perifosine, apatinib, vemurafenib, dabrafenib, trametinib, vismodegib, sonidegib, salinomycin, vintafolide, temsirolimus, everolimus, rituximab, trastuzumab, alemtuzumab, cetuximab, panitumumab, bevacizumab, trichostatin A, phenylbutyrate, sodium butyrate, valproic acid, suberoylanilide hydroxamic acid, belinostat, citarinostat, entinostat, mocetinostat, nanatinostat, panobinostat, pracinostat, romidepsin, tucidinostat, and vorinostat.

The containers suitable for housing the agent may be manufactured from a variety of materials such as glass, or plastic. The first container may house the present agent ABT-301 or a pharmaceutical formulation thereof, in an amount effective for treating colorectal cancer. The second container may house the anti-PD-lor anti-PD-L1 antibody or a pharmaceutical formulation thereof, in an amount effective for treating colorectal cancer. Alternatively or additionally, the kit may further comprise a third container housing a pharmaceutically acceptable excipient (e.g., a pharmaceutically acceptable buffer) therein, such as a phosphate-buffered saline (PBS), Ringer's solution, dextrose solution, and the like. It may further include other materials desirable from a commercial or user's standpoint, including other buffers, diluents, filters, needles, and syringes. The kit may further comprise a label or package insert on or associated with the containers. The label or package insert is typically a written instruction on a label or package insert (e.g., a paper sheet included in the kit), but the machine-readable instruction (e.g., instruction carried on a magnetic or optical storage disk) is also acceptable. The label or package insert indicates that the ABT-301, and the anti-PD-1 or anti-PD-L1 antibody respectively housed in the first and second containers are used for treating colorectal cancer. Also, the label or package insert may include directions for the administration of the ABT-301 and anti-PD-ior anti-PD-L1 antibody. The present pharmaceutical kit is provided in suitable packaging. Suitable packaging includes, but is not limited to, vials, bottles, jars, flexible packaging (e.g., sealed Mylar or plastic bags), boxes, etc.

2. The Method for Treating Colorectal Cancer

In another aspect of the present disclosure, the present invention is directed to a method of treating a subject in need thereof (e.g., a subject suffering from colorectal cancer, or a subject suspected of having colorectal cancer) by use of the present pharmaceutical kit. The method comprises the step of administering to the subject the present pharmaceutical kit, wherein the (E)-N-hydroxy-3-(1-(phenylsulfonyl)-indolin-5-yl)-acrylamide is administered to the subject in the amount of about 10 μg/kg-1 g/kg; and the anti-PD-1 or anti-PD-L1 antibody is administered to the subject in the amount of about 1 μg/kg-100 mg/kg.

Fundamentally, the present agent ABT-301 acts as a HDAC inhibitor that may induce colorectal cancer cell apoptosis, but also enhance the therapeutic effect of immunotherapy. According to some embodiments, the subject is a mouse, in which the ABT-301 is administered in the amount of 0.1 μg to 1 kg per kg of body weight of the subject per day (i.e., 0.1 μg-1 kg/kg/day). Preferably, the agent is administered in the amount of 1 μg-100 g/kg/day. More preferably, the agent is administered in the amount of 10 μg-10 g/kg/day. Even more preferably, the agent is administered in the amount of 0.1 mg-10 g/kg/day. Yet even more preferably, the agent is administered in the amount of 0.1 mg-1 g/kg/day. Still yet even more preferably, the agent is administered in the amount of 1 mg-1 g/kg/day. According to some working examples of the present disclosure, 25-100 mg/kg/day (e.g., 25, 50, or 100 mg/kg/day) of the ABT-301 is sufficient to induce colorectal cancer cell apoptosis, and to enhance the effectiveness of immunotherapy.

A skilled artisan could calculate the human equivalent dose (HED) for the agent ABT-301 based on the doses determined from animal models. Accordingly, the agent ABT-301 is administered to the human in the amount of 10 ng-100 g per kg of body weight of the subject per day (e.g., 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ng/kg/day; or 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ag/kg/day; or 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 mg/kg/day; or 1, 2, 3, 4, 5, 6, 7, 8, 9, 10, 20, 30, 40, 50, 60, 70, 80, 90, or 100 g/kg/day). Preferably, the agent ABT-301 is administered to the human in the amount of 100 ng-10 g/kg/day. More preferably, the agent ABT-301 is administered to the human in the amount of 1 μg-1 g/kg/day. Even more preferably, the agent ABT-301 is administered to the human in the amount of 10 μg-1 g/kg/day. Yet even more preferably, the agent ABT-301 is administered to the human in the amount of 10 μg-100 mg/kg/day. Still yet even more preferably, the agent ABT-301 is administered to the human in the amount of 0.1 mg-100 mg/kg/day. According to some working examples of the present disclosure, the agent ABT-301 is administered to the human in the amount of 2.5-10 mg/kg/day (e.g., 2.5, 5, or 10 mg/kg/day).

Depending on the desired purpose, the agent ABT-301 may be administered by any suitable route, for example, by enteral, oral, nasal, parenteral (such as intratumoral, intramuscular, intravenous, intraarterial, subcutaneous, intraperitoneal, intracerebral, intracerebroventricular or intrathecal injection), or transmucosal administration. According to one embodiment of the present disclosure, the agent ABT-301 is administered by oral.

For the purpose of inducing colorectal cancer cell apoptosis and/or enhancing the effectiveness of immunotherapy, the agent ABT-301 may be administered to the subject one or more times. For example, the agent ABT-301 may be administered once for a full course of treatment. Alternatively, the agent ABT-301 may be administered to the subject daily for at least 7 days; for example, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more days. In certain embodiments, when multiple doses are administered to a subject, the frequency of administering the multiple doses to the subject is three doses per day, two doses per day, one dose per day, one dose every other day, one dose every third day, one dose per week, one dose every other week, one dose per month, one dose every other month, one dose per season, one dose every half year, or one dose per year. In certain embodiments, the frequency of administering the multiple doses to the subject is one dose every day. In certain embodiments, the frequency of administering the multiple doses to the subject is two doses per week. In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject. In certain embodiments, the duration between the first dose and last dose of the multiple doses is about 1-1.5 months.

In accordance with the embodiments disclosed herein, the immunotherapy that may benefit from co-administration with agent ABT-301 comprises anti-PD-1 or anti-PD-L1 antibodies, as described above. According to some embodiments, the subject is a mouse, and the anti-PD-1 or anti-PD-L1 antibody is administered in the amount of 1 ng to 1 kg per kg of body weight of the subject per day (i.e., 1 ng-1 kg/kg/day). Preferably, the anti-PD-1 or anti-PD-L1 antibody is administered in the amount of 10 ng-100 g/kg/day. More preferably, the anti-PD-1 or anti-PD-L1 antibody is administered in the amount of 100 ng-10 g/kg/day. Even more preferably, the anti-PD-1 or anti-PD-L1 antibody is administered in the amount of 1 μg-10 g/kg/day. Yet even more preferably, the anti-PD-1 or anti-PD-L1 antibody is administered in the amount of 10 μg-1 g/kg/day. Still yet even more preferably, the anti-PD-1 or anti-PD-L1 antibody is administered in the amount of 100 μg-100 mg/kg/day. According to some working examples of the present disclosure, the anti-PD-1 or anti-PD-L1 antibody in the amount of 1 mg-10 mg/kg/day (e.g., 3.3 or 6.7 mg/kg/day) is sufficient to exhibit synergistic effect with the agent ABT-301 in treating colorectal cancer.

In the case when the subject is a human, the anti-PD-1 or anti-PD-L1 antibody is administered in the amount of 0.1 ng-100 g per kg of body weight of the subject per day (e.g., 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ng/kg/day; or 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 μg/kg/day; or 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 mg/kg/day; or 1, 2, 3, 4, 5, 6, 7, 8, 9, 10, 20, 30, 40, 50, 60, 70, 80, 90, or 100 g/kg/day). Preferably, the anti-PD-1 or anti-PD-L1 antibody is administered to the human in the amount of 1 ng-10 g/kg/day. More preferably, the anti-PD-1 or anti-PD-L1 antibody is administered to the human in the amount of 10 ng-1 g/kg/day. Even more preferably, the anti-PD-1 or anti-PD-L1 antibody is administered to the human in the amount of 100 ng-1 g/kg/day. Yet even more preferably, the anti-PD-1 or anti-PD-L1 antibody is administered to the human in the amount of 1 μg-100 mg/kg/day. Still yet even more preferably, the anti-PD-1 or anti-PD-L1 antibody is administered to the human in the amount of 10 μg-10 mg/kg/day. According to some working examples of the present disclosure, the anti-PD-1 or anti-PD-L1 antibody is administered to the human in the amount of 100 μg-1 mg/kg/day (e.g., 330 or 670 ag/kg/day).

Alternatively, the actual dosage of the present agent ABT-301 and the anti-PD-1 or anti-PD-L1 antibody may be determined by the attending physician based on the physical and physiological factors of the subject, these factors include, but are not limited to, age, gender, body weight, body surface, the disease to be treated, severity of the condition, previous history, the presence of other medications, the route of administration and etc.

Non-limiting routes of administration include, but are not limited to, enteral, oral, nasal, parenteral, topical or transmucosal administration, in which the parenteral administration can be any of intratumoral, intramuscular, intravenous, intraarterial, subcutaneous, intraperitoneal, intracerebral, intracerebroventricular or intrathecal injection. In one working example, the anti-PD-1 or anti-PD-L1 antibody is given to the subject via the intraperitoneal route.

As could be appreciated, the present agent ABT-301 may be administered to the subject prior to, concurrent with, or subsequent to the administration of the anti-PD-1 or anti-PD-L1 antibody, contingent upon medical considerations guided by healthcare professionals. For the purpose of treating colorectal cancer, the anti-PD-1 or anti-PD-L1 antibody may be administered to the subject one or more times. For example, the anti-PD-1 or anti-PD-L1 antibody may be administered once for a full course of treatment. Alternatively, the anti-PD-1 or anti-PD-L1 antibody may be administered to the subject daily for at least 7 days; for example, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more days. In certain embodiments, when multiple doses are administered to a subject, the frequency of administering the multiple doses to the subject is three doses per day, two doses per day, one dose per day, one dose every other day, one dose every third day, one dose per week, one dose every other week, one dose per month, one dose every other month, one dose per season, one dose every half year, or one dose per year. In certain embodiments, the frequency of administering the multiple doses to the subject is one dose every day. In certain embodiments, the frequency of administering the multiple doses to the subject is two doses per week. In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject. In certain embodiments, the duration between the first dose and last dose of the multiple doses is about 1-1.5 months.

The colorectal cancertreatable bythe present pharmaceutical kit and/or method may be a MSS-type or MSI-type colorectal cancer. Further, the colorectal cancer may be an in situ colorectal cancer or a metastatic colorectal cancer. Optionally, the colorectal cancer may be resistant to a chemotherapy (e.g., 5-fluorouracil (5-FU)), a radiation therapy (e.g., ultraviolet (UV) radiation), or an immunotherapy (e.g., adoptive immune cell therapy (AIT)). Accordingly, the present pharmaceutical kit and/or method provides a potential means to treat the colorectal cancer patient who has developed resistance to cancer therapies.

Optionally or in addition, the present method further comprises administering an additional anti-cancer treatment to the subject, prior to, in conjunction with, or subsequent to applying the present pharmaceutical kit to the subject, wherein the additional anti-cancer treatment is at least one of a surgery, a radiotherapy, a thermal therapy, an immunotherapy, a chemotherapy, or a targeted therapy. Exemplary agents utilized in immunotherapy, chemotherapy, or targeted therapy are as described above; for conciseness, their enumeration is omitted herein.

Alternatively, the present agent ABT-301 may be administered independently to the colorectal cancer patient without concomitant treatment (e.g., co-treatment or pre-treatment) with the anti-PD-1 or anti-PD-L1 antibody, which may still potentially achieve a discernible degree of efficacy in annihilating colorectal cancer; and vice versa.

Basically, the subject treatable by the present pharmaceutical kit and/or method is a mammal; preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

1. HDAC Enzymatic Activity Assay

For assessing the HDAC enzymatic activity of ABT-301, HDAC enzymatic activity assays were performed by using biochemical HDAC assays services platform offered by Reaction Biology Corp. (Malvern, PA, USA). The HDAC enzymatic activity assays were conducted by using a synthetic HDAC substrate, the structure of which was depicted in Formula (I). The moiety required for signal generation was linked to the carboxyl of the acetyllysine (K(Ac)), which serves as the target for deacetylation by the HDAC. After deacetylation by the HDAC, the fluorescent signaling group, 7-amino-4-methyl coumarin (AMC), can be quantified.

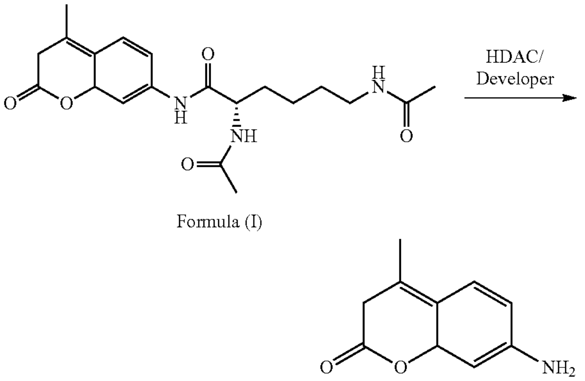

Formula (I)

Fluorescent Detection

Fluorogenic peptides that used to measure the enzymatic activity of HDAC were listed below in Table 1.

TABLE 1

Fluorogenic peptides used in the HDAC enzymatic activity assay

| HDAC target | Fluorogenic peptide substrates |
|---|---|
| HDAC 1, 2, 3, and 6 | Acetylated tetrapeptide comprising p53 residues 379-382: RHKK(Ac)-AMC (SEQ ID NO: 1) |
| HDAC 4, 5, 7, 9, and 11 | Trifluoroacetyl lysine |
| HDAC 8 | Twice acetylated tetrapeptide comprising p53 residues 379-382: RHK(Ac)K(Ac)-AMC (SEQ ID NO: 2) |
| HDAC 10 | Acetylated polyamine: Ac-Spermidine-AMC |

Histone deacetylase activity was detected by fluorigenic release of AMC from the aforementioned fluorogenic peptide substrates upon deacetylase enzymatic activity. Half maximal inhibitory concentration ($IC_{50}$) was determined at the drug concentration that results in a 50% reduction in the increase of HDAC activity observed in control wells during the compound incubation in 10-dose $IC_{50}$ format. Controls: No inhibitor control (DMSO vehicle only), and for every target, one target-specific control compound was tested in 10-dose $IC_{50}$ format. HDAC reference compounds: (1) trichostatin A (TSA), a target-specific control compound for HDAC 1, 2, 3, 6, 8, and 11; (2) TMP269, a target-specific control compound for HDAC 4, 5, 7, and 9; and (3) quisinostat, a target-specific control compound for HDAC 10.

2. Cell Culture

CT26.WT cells (ATCC No.: CRL-2638™), mouse colon carcinoma cells typically classified as microsatellite stable, were maintained in RPMI supplemented with 10% fetal bovine serum, 100 U/mL penicillin, 100 μg/mL streptomycin, 10 mM HEPES, and 1 mM sodium pyruvate. MC-38 cells (purchased from Kerafast, Inc.), derived from C57BL/6 murine colon adenocarcinoma cells typically classified as microsatellite instable, were maintained in DMEM with 10% fetal bovine serum, 100 U/mL penicillin, 100 μg/mL streptomycin, 10 mM HEPES, and 1× nonessential amino acid. All the cells were maintained in a humidified atmosphere having 5% $CO_2$ at 37° C.

3. Animals

Female BALB/c mice (BALB/cByJNarl) aged 5-7 weeks (for CT26 subcutaneous tumor model), and female C57BL/6 mice (C57BL/6JNarl) aged 5-7 weeks (for MC-38 subcutaneous tumor model), were housed in standard cages within the animal facility at the Industrial Technology Research Institute (ITRI). A one-week acclimatization period preceded the commencement of the study, with the health of the mice monitored daily. Animals were kept in rooms at 22-26° C. with 40-70% humidity, positive pressure, 60% air recirculation, ventilation rate 15-20 changes per hour, and a controlled light-dark cycle (12-12 hours).

4. CT26 Subcutaneous Tumor Model

CT26 cells ($2 \times 10^5$) were suspended in 100 μl of PBS and subcutaneously inoculated into the right flank of female BALB/c mice. Tumors were measured with calipers, and tumor size was calculated as follows: tumor volume (V)=$(L \times S^2)/2$ (L, longest diameter, mm; S, shortest diameter, mm). Tumor size and body weight of mice were monitored and recorded twice to thrice per week. The antitumor activities of treatments were expressed as percentages of tumor growth inhibition (% TGI), as calculated using the following formula: [1−(final tumor volume−initial tumor volume for treated group)/(final tumor volume−initial tumor volume for vehicle group)]×100. Body weight of each mouse was also compared to that on the first day of treatment (Day 0) and expressed as a percentage of Day 0 value. All procedures were performed in accordance with the Guide for the Care and Use of Laboratory Animals (NRC, USA) and approved by the Institutional Animal Care & Use Committee (IACUC) of ITRI (IACUC approval No.: ITRI-IACUC-2022-031, ITRI-IACUC-2023-031, and ITRI-IACUC-2023-010).

4-1. A Single Dose of ABT-301, with or without Combination with Avelumab

The administration of treatments commenced five days following the inoculation of CT26 cells, with the day of treatment initiation designated as Day 0. When mean tumor volume reached 50-100 $mm^3$, the mice were assigned into four groups through S-type grouping according to tumor size. The four groups included: (1) vehicle; (2) Avelumab (100 μg, intraperitoneal (IP), biweekly (BIW, twice per week)); (3) ABT-301 (100 mg/kg, per os (PO, oral), quaque die (QD, once every day)); and (4) ABT-301 (100 mg/kg, PO, QD)+Avelumab (100 μg, IP, BIW). Eight mice were used in each group. Treatments were administered for 43 days. ABT-301 was prepared with 0.5% carboxymethyl cellulose+0.1% Tween 80 in 5% dextrose. Avelumab was prepared with PBS. The treatment plans are summarized in Table 2.

TABLE 2

| Treatment plans for a single dose of ABT-301 w/wo avelumab | | | | | |
|---|---|---|---|---|---|
| Group | Treatment | Dose | Dosing frequency | Route | No. of Animals |
| 1 | Vehicle* | — | QD | PO | 8 |
| 2 | Avelumab | 100 μg | BIW | IP | 8 |
| 3 | ABT-301 | 100 mg/kg | QD | PO | 8 |
| 4 | ABT-301 + Avelumab | 100 mg/kg + 100 μg | QD/BIW | PO/IP | 8 |

*Vehicle control: 0.5% carboxymethyl cellulose + 0.1% Tween 80 in 5% dextrose.

4-2. Multiple Doses of ABT-301, with or without Combination with Avelumab

When mean tumor volume reached about 80-100 $mm^3$, treatments were initiated and the day of treatment initiation was designated as Day 0. The mice were assigned into eight groups, including: (1) vehicle; (2) Avelumab (200 μg, IP, BIW); (3) ABT-301 (25 mg/kg, PO, QD); (4) ABT-301 (25 mg/kg, PO, QD)+Avelumab (200 μg, IP, BIW); (5) ABT-301 (50 mg/kg, PO, QD); (6) ABT-301 (50 mg/kg, PO, QD)+Avelumab (200 μg, IP, BIW); (7) ABT-301 (100 mg/kg, PO, QD); and (8) ABT-301 (100 mg/kg, PO, QD)+Avelumab (200 μg, IP, BIW). Treatments were administered for indicated period (24 days) or until humane endpoints. Ten mice were used in each group. ABT-301 was prepared with 0.5% carboxymethyl cellulose+0.1% Tween 80 in 5% dextrose. Avelumab was prepared with PBS. The treatment planes are summarized in Table 3.

TABLE 3

| Treatment plans for multiple doses of ABT-301 with avelumab | | | | | | |
|---|---|---|---|---|---|---|
| Group | Treatments | Dose | Dosing frequency | Route | Dosing period | No. of Animals |
| 1 | Vehicle* | — | QD | PO | 24 days | 10 |
| 2 | Avelumab# | 200 μg | BIW# | IP | 24 days | 10 |
| 3 | ABT-301 | 25 mg/kg | QD | PO | 24 days | 10 |
| 4 | ABT-301 + Avelumab# | 25 mg/kg + 200 μg | QD/BIW# | PO/IP | 24 days | 10 |
| 5 | ABT-301 | 50 mg/kg | QD | PO | 24 days | 10 |
| 6 | ABT-301 + Avelumab# | 50 mg/kg + 200 μg | QD/BIW# | PO/IP | 24 days | 10 |
| 7 | ABT-301 | 100 mg/kg | QD | PO | 24 days | 10 |
| 8 | ABT-301 + Avelumab# | 100 mg/kg + 200 μg | QD/BIW# | PO/IP | 24 days | 10 |

*Vehicle control: 0.5% carboxymethyl cellulose + 0.1% Tween 80 in 5% dextrose.
#Avelumab was administrated on Day 0, 3, 7 and 10.

4-3. Multiple Doses of ABT-301, with or without Combination with RMP1-14

When mean tumor volume reached about 80-100 $mm^3$, treatments were initiated and the day of treatment initiation was assigned as Day 0. The mice were assigned into eight groups, including: (1) vehicle; (2) RMP1-14 (200 μg, IP, BIW); (3) ABT-301 (25 mg/kg, PO, QD); (4) ABT-301 (25 mg/kg, PO, QD)+RMP1-14 (200 μg, IP, BIW); (5) ABT-301 (50 mg/kg, PO, QD); (6) ABT-301 (50 mg/kg, PO, QD)+RMP1-14 (200 μg, IP, BIW); (7) ABT-301 (100 mg/kg, PO, QD); and (8) ABT-301 (100 mg/kg, PO, QD)+RMP1-14 (200 μg, IP, BIW). Treatments were administered for indicated period (27 days) or until humane endpoints. Ten mice were used in each group. ABT-301 was prepared with 0.5% carboxymethyl cellulose+0.1% Tween 80 in 5% dextrose. RMP1-14 was prepared with PBS. The treatment plans are summarized in Table 4.

TABLE 4

| Treatment plans for multiple doses of ABT-301 with RMP1-14 | | | | | | |
|---|---|---|---|---|---|---|
| Group | Treatments | Dose | Dosing frequency | Route | Dosing period | No. of Animals |
| 1 | Vehicle* | — | QD | PO | 27 days | 10 |
| 2 | RMP1-14 | 200 μg | BIW | IP | 27 days | 10 |
| 3 | ABT-301 | 25 mg/kg | QD | PO | 27 days | 10 |
| 4 | ABT-301 + RMP1-14 | 25 mg/kg + 200 μg | QD/BIW | PO/IP | 27 days | 10 |
| 5 | ABT-301 | 50 mg/kg | QD | PO | 27 days | 10 |
| 6 | ABT-301 + RMP1-14 | 50 mg/kg + 200 μg | QD/BIW | PO/IP | 27 days | 10 |
| 7 | ABT-301 | 100 mg/kg | QD | PO | 27 days | 10 |
| 8 | ABT-301 + RMP1-14 | 100 mg/kg + 200 μg | QD/BIW | PO/IP | 27 days | 10 |

*Vehicle control: 0.5% carboxymethyl cellulose + 0.1% Tween 80 in 5% dextrose.

4-4. HDAC Inhibitors, with or without Combination with RMP1-14

HDAC inhibitors including ABT-301, Vorinostat, and Citarinostat were used in the present study. When mean tumor volume reached about 80-100 $mm^3$, treatments were initiated and the day of treatment initiation was designated as Day 0. The mice were randomly assigned into eight groups, including: (1) vehicle; (2) RMP1-14 (200 µg, IP, BIW); (3) ABT-301 (100 mg/kg, PO, QD); (4) ABT-301 (100 mg/kg, PO, QD)+RMP1-14 (200 µg, IP, BIW); (5) Vorinostat (100 mg/kg, PO, QD); (6) Vorinostat (100 mg/kg, PO, QD)+RMP1-14 (200 µg, IP, BIW); (7) Citarinostat (50 mg/kg, IP, QD); and (8) Citarinostat (50 mg/kg, IP, QD)+RMP1-14 (200 µg, IP, BIW). Treatments were administered for indicated period (31 days) or until humane endpoints. Eight or nine mice were used in each group. ABT-301 and Vorinostat were prepared with 0.5% carboxymethyl cellulose+0.1% Tween 80 in 5% dextrose. Citarinostat was prepared 10% DMSO, 40% PEG300, 5% Tween-80, and 45% saline. RMP1-14 was prepared with PBS. The treatment plans are summarized in Table 5.

TABLE 5

Treatment plans for different HDAC inhibitors with RMP1-14

| Group | Treatments | Dose | Dosing frequency | Route | Dosing period | No. of Animals |
|---|---|---|---|---|---|---|
| 1 | Vehicle* | — | QD | PO | 31 days | 8 |
| 2 | RMP1-14 | 200 µg | BIW | IP | 31 days | 8 |
| 3 | ABT-301 | 100 mg/kg | QD | PO | 31 days | 9 |
| 4 | ABT-301 + RMP1-14 | 100 mg/kg + 200 µg | QD/BIW | PO/IP | 31 days | 9 |
| 5 | Vorinostat | 100 mg/kg | QD | PO | 31 days | 8 |
| 6 | Vorinostat + RMP1-14 | 100 mg/kg + 200 µg | QD/BIW | PO/IP | 31 days | 9 |
| 7 | Citarinostat | 50 mg/kg | QD | IP | 31 days | 9 |
| 8 | Citarinostat + RMP1-14 | 50 mg/kg + 200 µg | QD/BIW | IP/IP | 31 days | 9 |

*Vehicle control: 0.5% carboxymethyl cellulose + 0.1% Tween 80 in 5% dextrose.

5. MC-38 Subcutaneous Tumor Model

MC-38 cells ($2\times10^5$) were suspended in 100 µl of PBS and subcutaneously inoculated into the right flank of female C57BL/6 mice. Tumors were measured with calipers, and tumor size was calculated as follows: tumor volume (V)=$(LxS^2)/2$ (L, longest diameter, mm; S, shortest diameter, mm). Tumor size and body weight of mice were monitored and recorded twice to thrice per week. The antitumor activities of treatments were expressed as percentages of tumor growth inhibition (% TGI), as calculated using the following formula: [1−(final tumor volume−initial tumor volume for treated group)/(final tumor volume−initial tumor volume for vehicle group)]×100. Body weight of each mouse was also compared to that on the first day of treatment (Day 0) and expressed as a percentage of Day 0 value. All procedures were performed according to the Guide for the Care and Use of Laboratory Animals (NRC, USA) and approved by the IACUC of ITRI (IACUC approval No.: ITRI-IACUC-2023-003).

5-1. A Single Dose of ABT-301, with or without Combination with Avelumab or RMP1-14

Treatments were initiated 6 days after inoculation of MC-38 cells and the day of treatment initiations was assigned as Day 0. When mean tumor volume reached 50-100 $mm^3$, the mice were assigned into six groups through S-type grouping according to tumor size. The six groups included: (1) vehicle; (2) ABT-301 (100 mg/kg, PO, QD); (3) Avelumab (200 µg, IP, BIW); (4) ABT-301 (100 mg/kg, PO, QD)+Avelumab (100 µg, IP, BIW); (5) RMP1-14 (200 µg, IP, BIW); and (6) ABT-301 (100 mg/kg, PO, QD)+RMP1-14 (200 µg, IP, BIW). Treatments were administered for indicated period (29 or 36 days) or until humane endpoints. Eight mice were used in each group. ABT-301 was prepared with 0.5% carboxymethyl cellulose+0.1% Tween 80 in 5% dextrose. Avelumab and RMP1-14 were prepared with PBS. The treatment plans are summarized in Table 6.

TABLE 6

Treatment plans for a single dose of ABT-301 with avelumab or RMP1-14

| Group | Treatment | Dose | Dosing frequency | Route | Dosing period | No. of Animals |
|---|---|---|---|---|---|---|
| 1 | Vehicle* | — | QD | PO | 29 days | 8 |
| 2 | ABT-301 | 100 mg/kg | QD | PO | 29 days | 8 |
| 3 | Avelumab | 200 µg | BIW | IP | 29 days | 8 |

TABLE 6-continued

Treatment plans for a single dose of ABT-301 with avelumab or RMP1-14

| Group | Treatment | Dose | Dosing frequency | Route | Dosing period | No. of Animals |
|---|---|---|---|---|---|---|
| 4 | ABT-301 + Avelumab | 100 mg/kg + 200 μg | QD/BIW | PO/IP | 29 days | 8 |
| 5 | RMP1-14 | 200 μg | BIW | IP | 36 days | 8 |
| 6 | ABT-301 + RMP1-14 | 100 mg/kg + 200 μg | QD/BIW | PO/IP | 36 days | 8 |

*Vehicle control: 0.5% carboxymethyl cellulose + 0.1% Tween 80 in 5% dextrose.

6. Statistical Analysis

Graphical and data analysis were processed with Excel and GraphPad Prism. Statistical analysis was performed using GraphPad Prism. Statistical significance was analyzed using the Student's t-test or one-way ANOVA. P-value <0.05 indicates a statistically significant difference.

Example 1 Characterization the HDAC Inhibition Activity of ABT-301

In the present example, the principal objective is to understand the profile of the HDAC enzymatic activity exhibited by ABT-301. The procedures for evaluating the HDAC enzymatic activity were as described in the "Materials and Methods" section, and the results are presented in Table 7. Based on the findings, ABT-301 clearly demonstrated HDAC enzymatic activity towards HDAC1, HDAC2, and HDAC3 (categorized within HDAC class I), as well as HDAC6 and HDAC10 (classified under HDAC class IIb). However, ABT-301 did not manifest activity towards HDAC4, HDAC5, HDAC7, and HDAC9 (falling within HDAC class IIa) or HDAC11 (pertaining to HDAC class IV). These results evidently suggest that ABT-301 functions as an inhibitor for HDAC class I and IIb.

TABLE 7

The HDAC enzymatic activity of ABT-301 ($IC_{50}$ (nM))

| Target | | Compound | | |
|---|---|---|---|---|
| | | ABT-301 | Vorinostat | Tucidinostat |
| HDAC Class I | HDAC1 | 30.24 | 86.9 | 102.8 |
| | HDAC2 | 93.17 | 229.5 | 133.2 |
| | HDAC3 | 6.61 | 43.5 | 106.9 |
| | HDAC8 | 956.3 | 1133 | >3000 |
| HDAC Class IIa | HDAC4 | >3000 | >3000 | >3000 |
| | HDAC5 | >3000 | >3000 | >3000 |
| | HDAC7 | >3000 | >3000 | >3000 |
| | HDAC9 | >3000 | >3000 | >3000 |
| HDAC Class IIb | HDAC6 | 53.19 | 3.61 | >3000 |
| | HDAC10 | 59.68 | 283.9 | >3000 |
| HDAC Class IV | HDAC11 | 994.4 | >3000 | >3000 |

In the HDAC enzymatic study, vorinostat and tucidinostat were additionally incorporated for comparative analysis in parallel with ABT-301; these two compounds belong to inhibitors of HDAC Class I and/or IIb. Notwithstanding, ABT-301 generally evinced superior inhibition activity against those HDACs within HDAC Class I and/or IIb.

Example 2 Effects of ABT-301 on the Inhibition of MSS Subtype Colorectal Cancer 2.1 Initial Evaluation of ABT-301 with Combination with Avelumab In the instant example, the primary objective is to evaluate the anti-cancer effects of ABT-301 on the MSS subtype colorectal cancer, as well as its capacity to potentiate the efficacy of immunotherapy against the MSS subtype colorectal cancer, as this subtype constitutes the majority (approximately 90%) of colorectal cancer patients.

To this end, an initial study was effectuated in accordance with the procedures delineated in the section of "4-1. A single dose of ABT-301, with or without combination with avelumab" of the "Materials and Methods," in which the immunotherapy was achieved by administering avelumab to the animal, and the results are as depicted in FIGS. 1A-1G. The results of tumor growth in CT26-bearing mice are delineated in FIGS. 1A-1D, which focused on depicting the complete response (CR) for the indicated treatments against the tumor growth in the mice. Pursuant to the results, as compared to the vehicle group, administering avelumab or ABT-301 alone to the mice did not substantially increase the number of the mice exhibiting the CR to the tumor (i.e., the CR rates for the vehicle, the avelumab, and the ABT-301 groups were 0/8, 1/8, and 2/8, respectively), whereas the combined administration of avelumab and ABT-301 significantly enhanced the CR rate in the treated mice (the CR rate for the combined treatment group was 7/8).

Figure 1E:
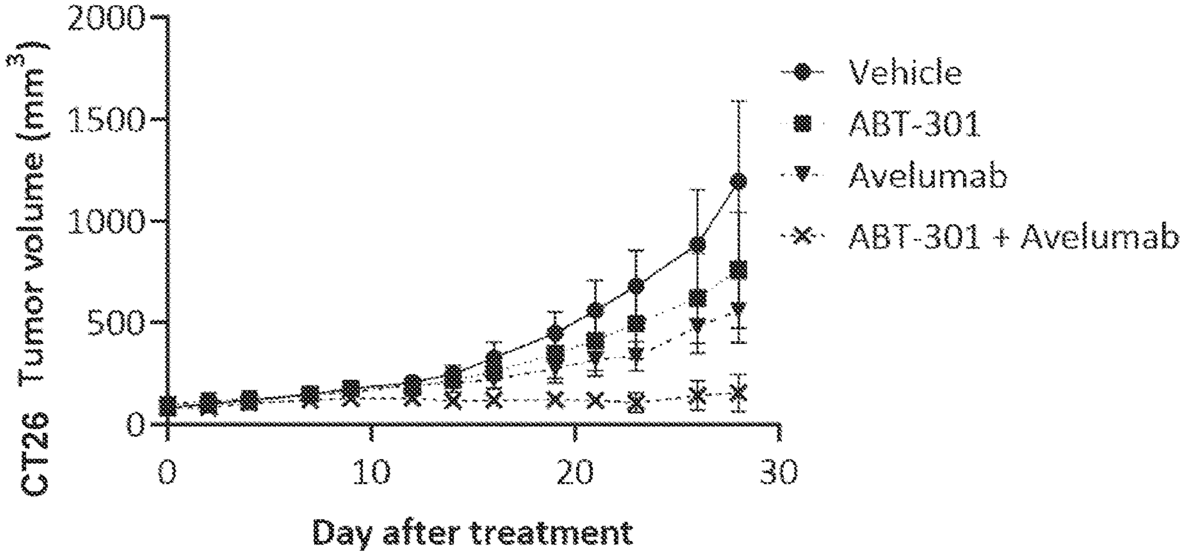
Figure 1F:
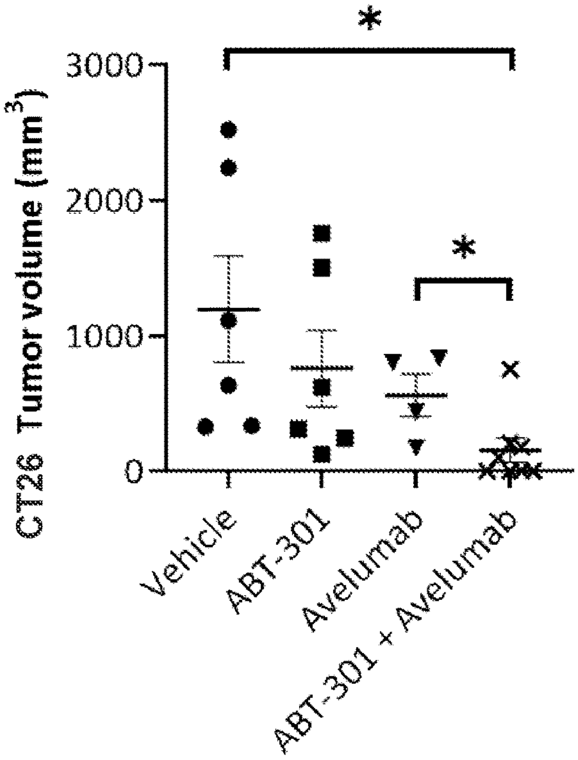

The results for the tumor volume documented for 28 days and on Day 28 are presented in FIGS. 1E-1F and Table 8, in which ABT-301 and avelumab respectively demonstrated anti-tumor activity in differing levels, however, the combined therapy exhibited the maximum extent suppression of the tumor growth. Meanwhile, there was no significant difference of body weight (%) on Day 28 between each treatment group and vehicle group as observed (data not shown).

TABLE 8

Tumor size and tumor growth inhibition of CT26 allograft tumor mice following ABT-301 and avelumab treatments on Day 28

| Groups | Day 28 after treatments | |
|---|---|---|
| | Tumor size ($mm^3$) | TGI (%) |
| Vehicle | 1195.69 ± 394.59 | — |
| Avelumab (IP, 100 μg) | 559.63 ± 156.94 | 58.51 ± 14.14 |

TABLE 8-continued

Tumor size and tumor growth inhibition of CT26 allograft tumor mice following ABT-301 and avelumab treatments on Day 28

| Groups | Day 28 after treatments Tumor size ($mm^3$) | TGI (%) |
|---|---|---|
| ABT-301 (PO, 100 mg/kg) | 759.26 ± 285.30 | 39.34 ± 26.01 |
| ABT-301 (PO, 100 mg/kg) + Avelumab (IP, 100 μg) | 154.35 ± 90.28* | 93.61 ± 8.37 |

The data are presented as means ± SEM. The dead mice and mice reaching humane endpoints were excluded. n = 6 for vehicle group, n = 6 for ABT-301 group, n = 4 for Avelumab group, and n = 8 for ABT-301 + Avelumab group.
*$P < 0.05$ compared to Avelumab group by t-test.

Figure 1G:
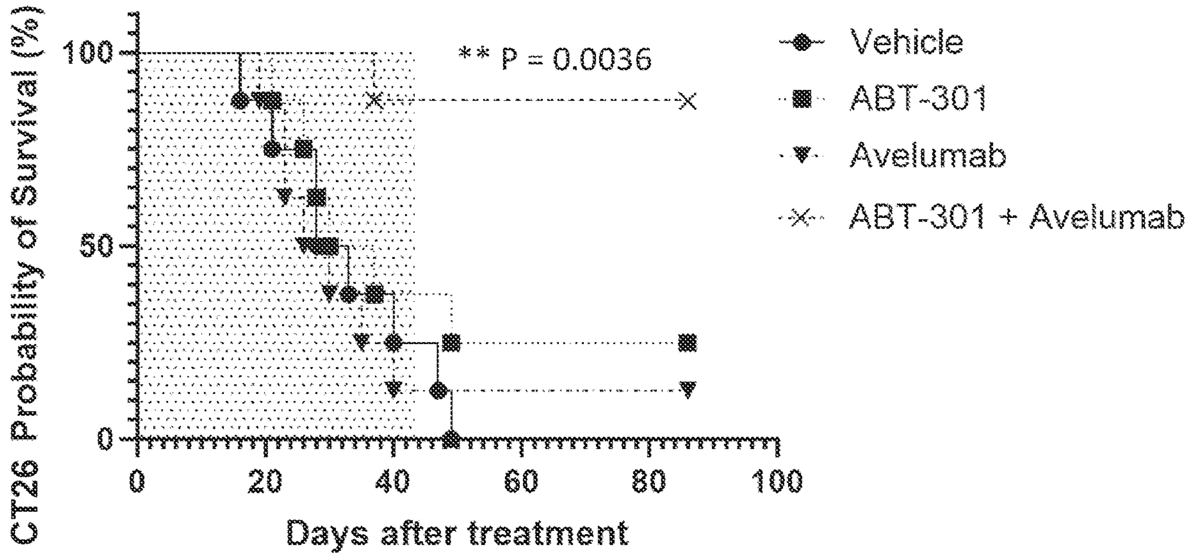

Additionally, the combined therapy largely increased the survival rate of the treated mice, as compared to the mice in the vehicle, the avelumab, and the ABT-301 treatment groups (FIG. 1G and Table 9). Taken together, albeit ABT-301 and avelumab alone may exhibit anti-cancer activity, the combination treatment of ABT-301 and avelumab could strongly potentiate the anti-tumor growth effects of avelumab on CT26 tumors, as reflected by the CR to the tumor growth and the suppression of the tumor volume. Moreover, ABT-301 and avelumab combination treatment could prolong the survival of the CT26-bearing mice when compared to ABT-301 or avelumab treatment alone.

TABLE 9

Median survival of CT26 allograft tumor mice following ABT-301 and Avelumab treatments over the entire study

| (Day) | Vehicle | Avelumab | ABT-301 | ABT-301 + Avelumab |
|---|---|---|---|---|
| Median survival | 30.5 | 28 | 33.5 | >86 |

2.2 Further Evaluation of ABT-301 with Combination with Avelumab

Figure 2A:
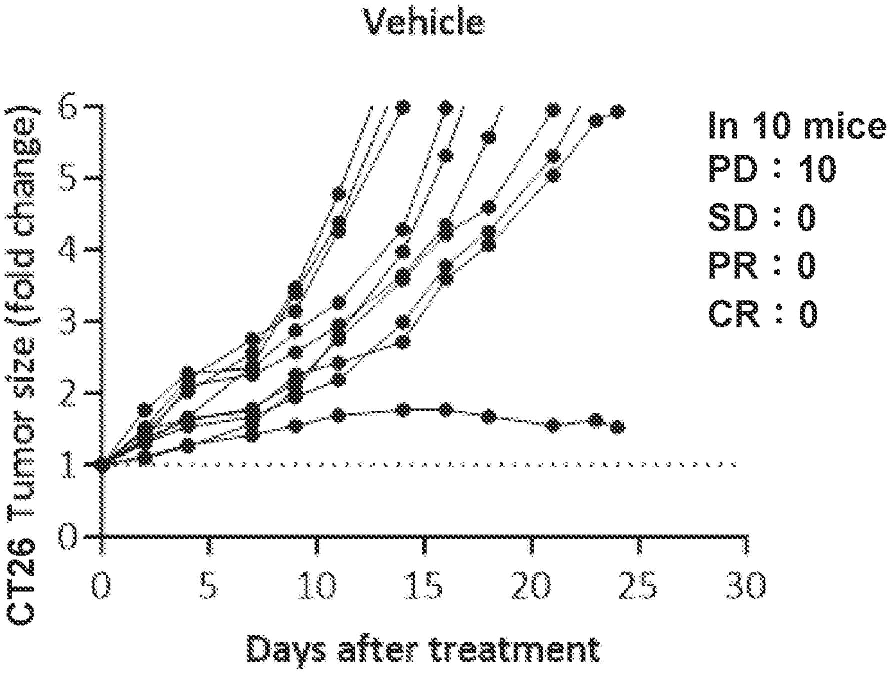
FIGS. 2A-2J are the results of treating mice bearing CT26 with a combination of ABT-301 and avelumab, in which FIGS. 2A-2H respectively illustrate the number of mice exhibiting a progressive disease (PD), a stable disease (SD), a partial response (PR), or a complete response (CR) in the indicated treatment groups (n=10/group)
Figure 2B:
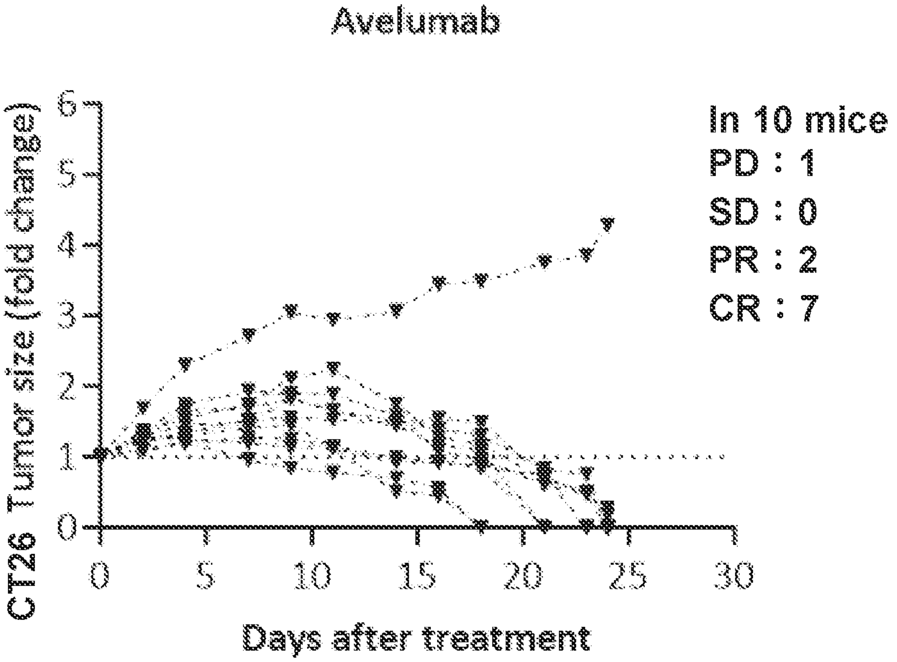
Figure 2C:
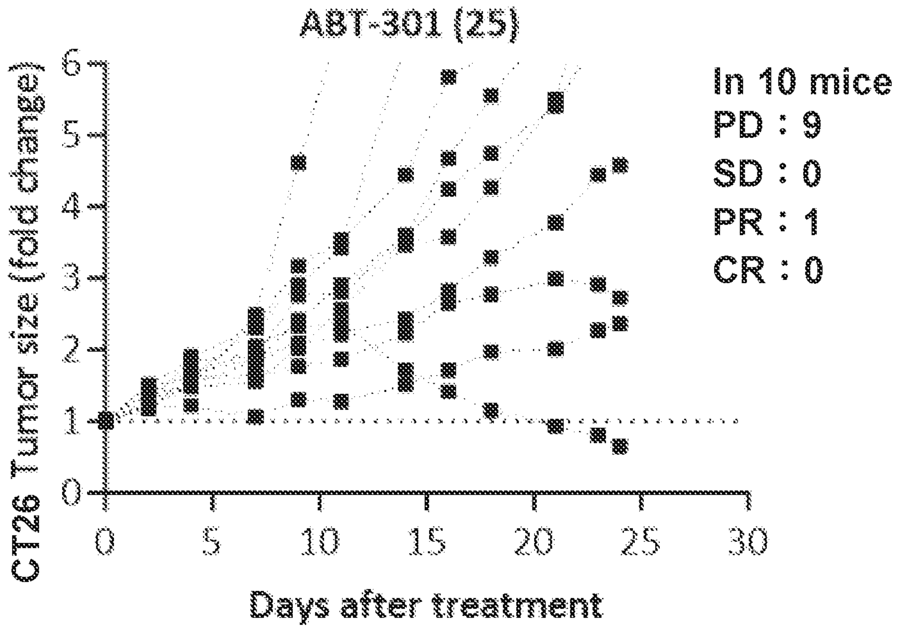
Figure 2D:
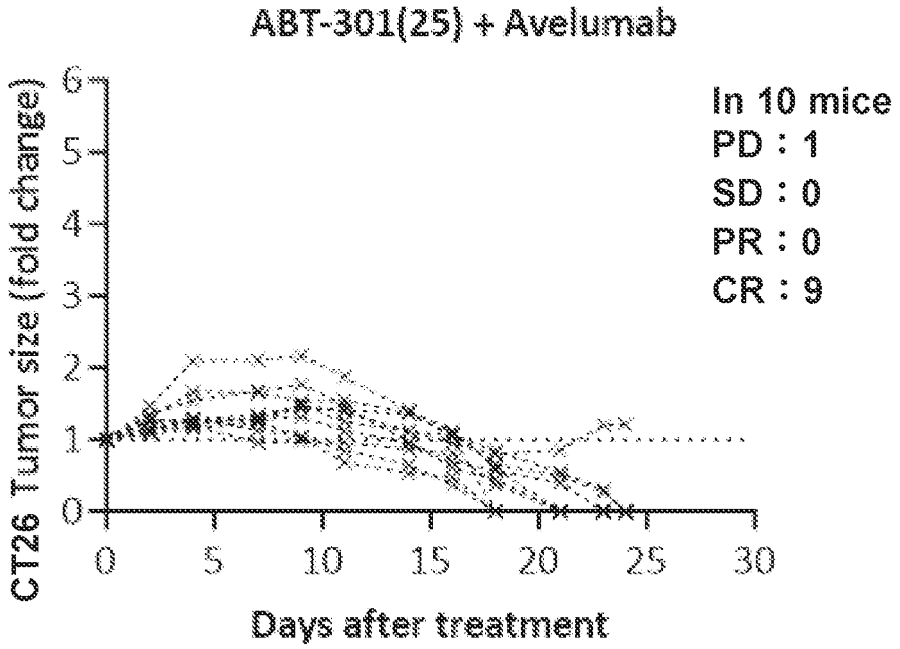
Figure 2E:
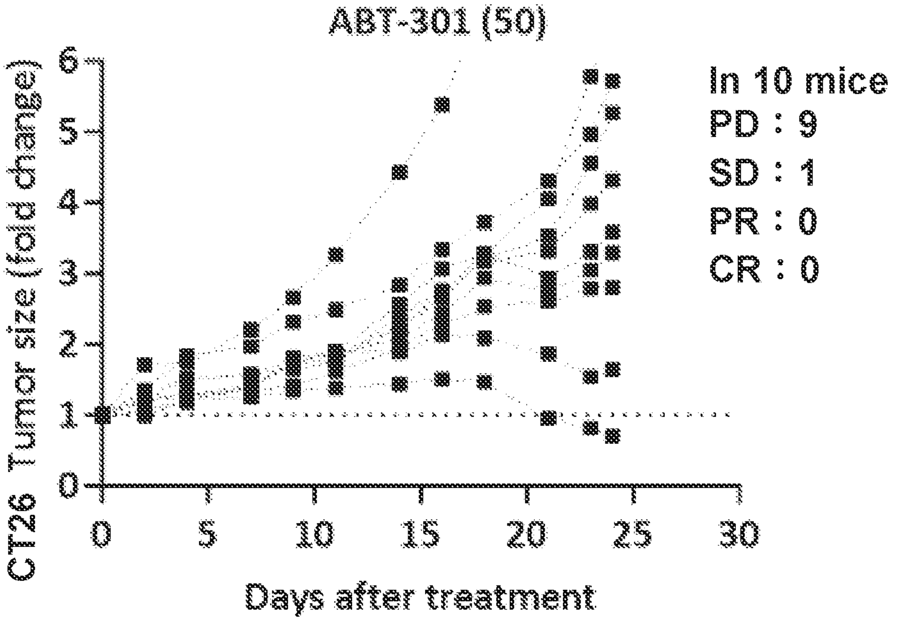
Figure 2F:
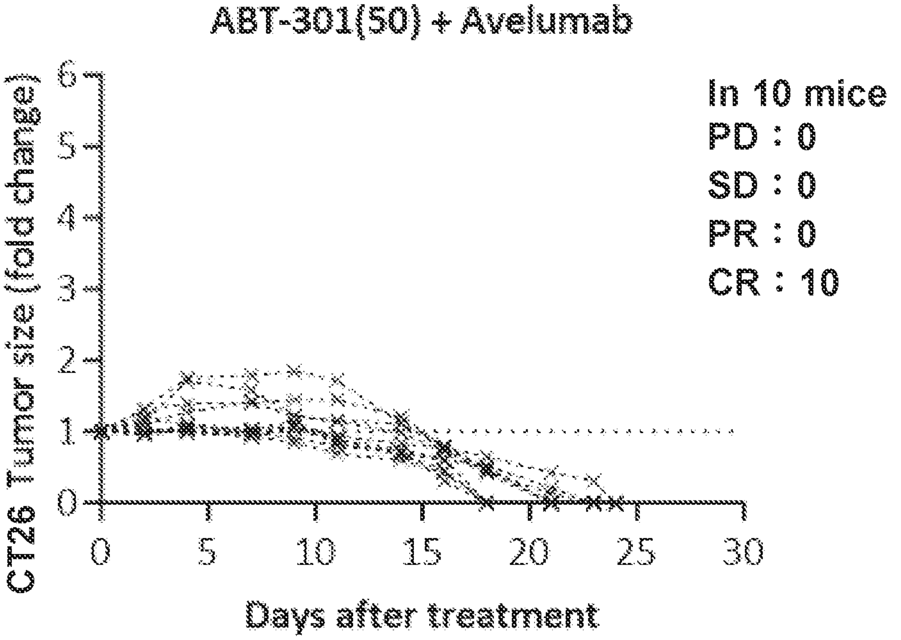
Figure 2G:
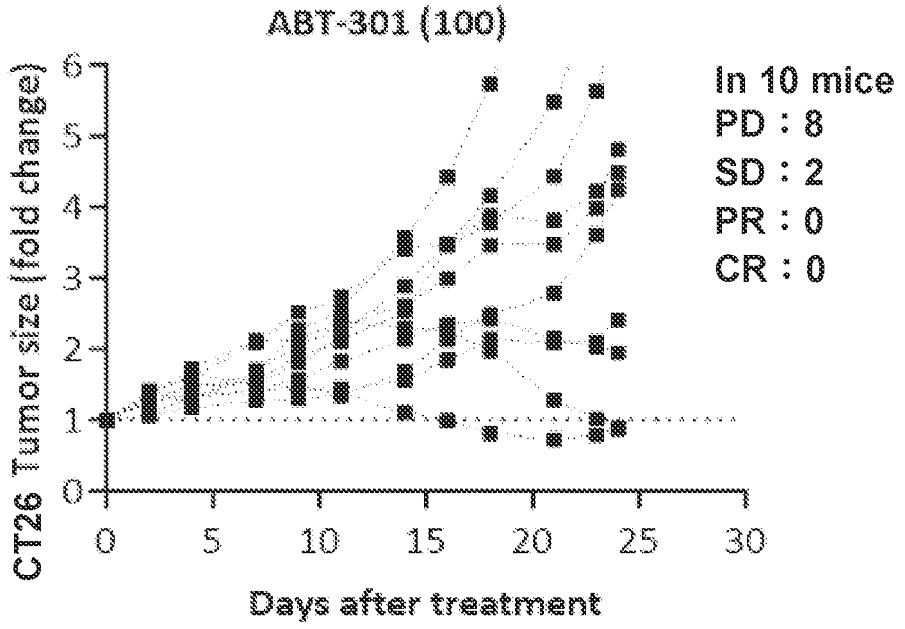
Figure 2H:
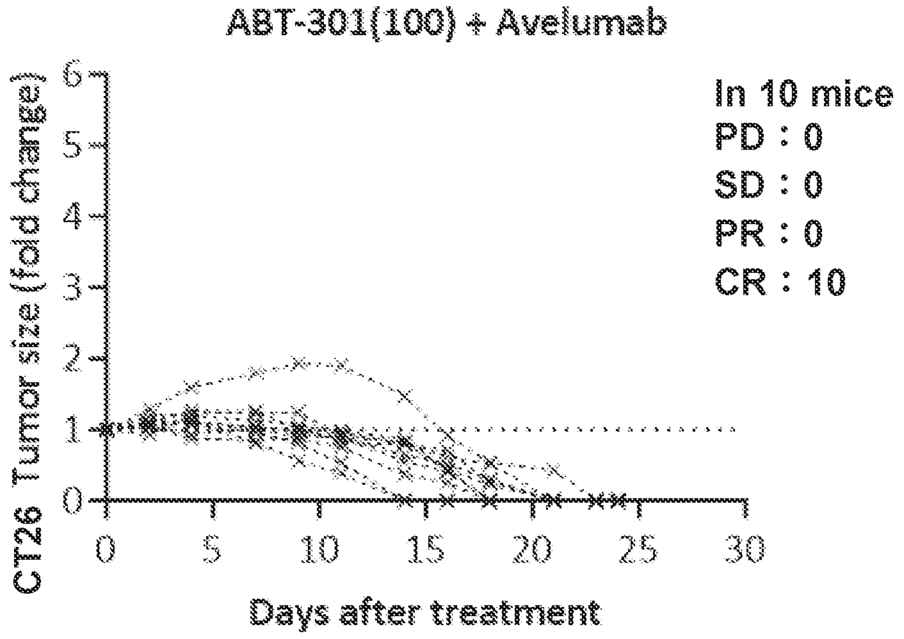

Based on the knowledge acquired from Example 2.1, the study for investigating the ability of ABT-301 in cancer inhibition and the capacity of ABT-301 in potentiating the avelumab in treating colorectal cancer is further extended to multiple dosages of ABT-301 with or without combination with avelumab. The procedures were as delineated in the section of "4-2. Multiple doses of ABT-301, with or without combination with avelumab" of the "Materials and Methods," and the results are provided in FIGS. 2A-2J. According to FIGS. 2A-2H, in comparison to the vehicle group (FIG. 2A), while administration of avelumab alone may yield some degree of anti-cancer activity, as indicated by the complete response (CR) rate (i.e., 7 mice exhibited CR in the avelumab group out of 10 mice; FIG. 2B), the incremental increase in ABT-301 dose from 25 mg/kg to 100 mg/kg only marginally enhanced treatment efficacy (i.e., from PD=9 and PR=1 in the ABT-301 (25) group, to PD=8 and SD=2 in the ABT-301 (100) group; FIGS. 2C, 2E, and 2G). Nevertheless, the combination of ABT-301 and avelumab significantly enhanced the CR of the treated mice to the tumor, even at the minimal dosage of ABT-301 as low as 25 mg/kg (FIGS. 2C vs. 2D, FIGS. 2E vs. 2F, and FIGS. 2G vs. 2H). Moreover, the combination therapy yet demonstrated a dose-dependent treatment efficacy with increasing ABT-301 dosage (i.e., from PD=1 and CR=9 in the ABT-301 (25)+avelumab group, to CR=10 in the ABT-301 (100)+avelumab group; FIGS. 2D, 2F, and 2H).

Figure 2I:
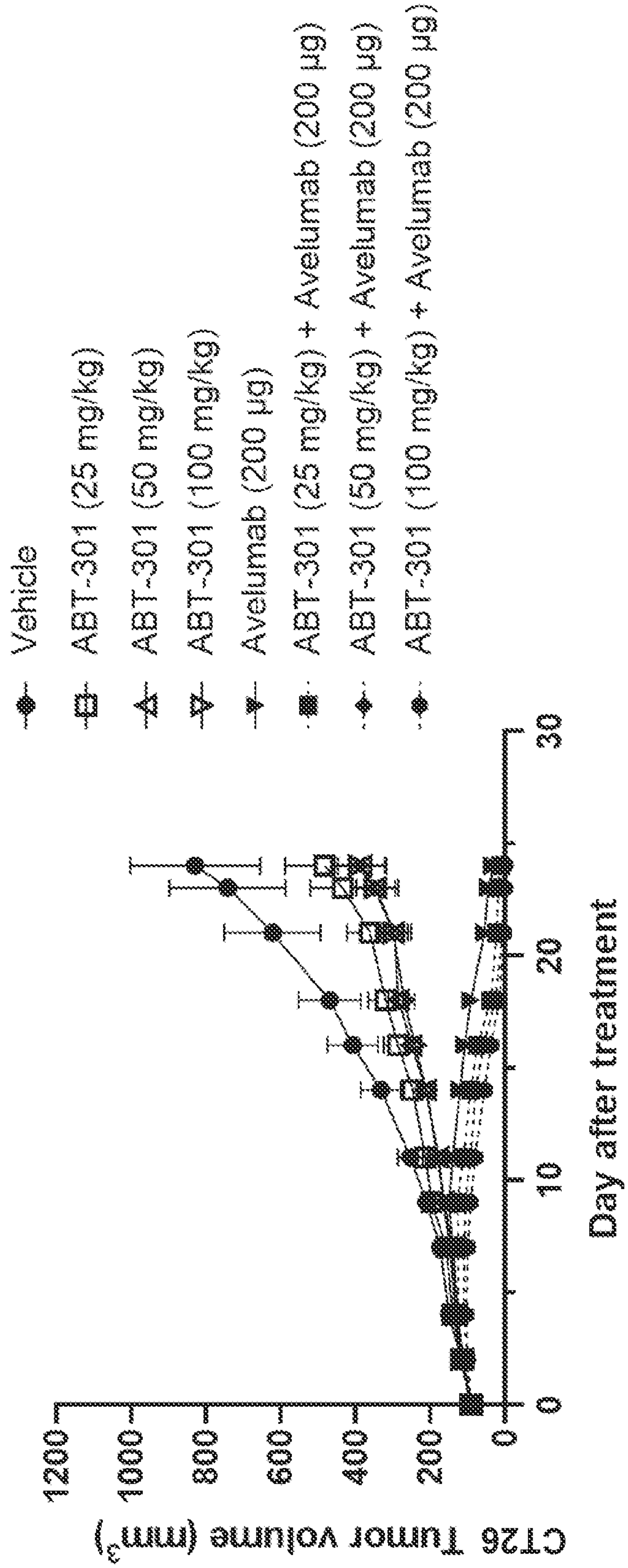
Figure 2J:
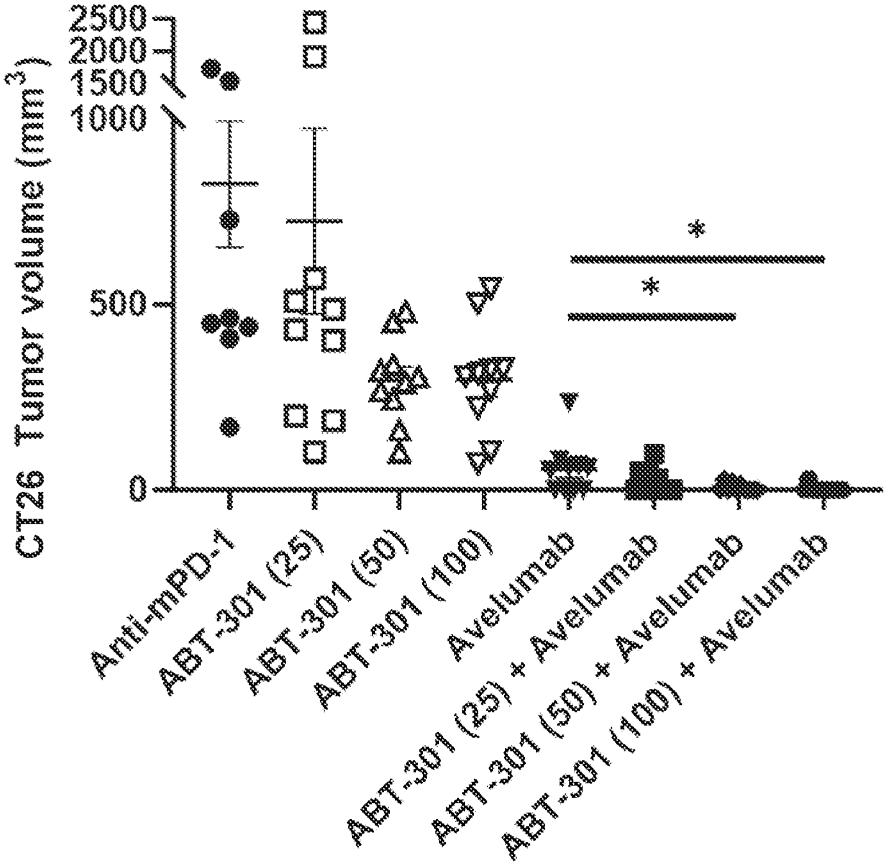

The results for the tumor volume recorded for 24 days and on Day 21 are presented in FIGS. 2I-2J and Table 10, in which ABT-301 and avelumab respectively demonstrated anti-tumor activity in differing levels, however, the combined therapy further suppressed tumor growth. Meanwhile, there was no significant difference of body weight (%) on Day 24 between each treatment group and vehicle group as observed (data not shown).

TABLE 10

Tumor size of CT26 allograft tumor mice following ABT-301 and avelumab treatments on Day 24

| Groups | Day 24 after treatments Tumor size ($mm^3$) |
|---|---|
| Vehicle | 829.98 ± 174.13 |
| Avelumab (200 μg) | 31.79 ± 26.66** |
| ABT-301 (25 mg/kg) | 482.19 ± 106.55 |
| ABT-301 (25 mg/kg) + Avelumab (200 μg) | 13.73 ± 13.73** |
| ABT-301 (50 mg/kg) | 384.31 ± 62.20* |
| ABT-301 (50 mg/kg) + Avelumab (200 μg) | 0 ± 0** |
| ABT-301 (100 mg/kg) | 391.42 ± 73.97* |
| ABT-301 (100 mg/kg) + Avelumab (200 μg) | 0 ± 0** |

The data are presented as means ± SEM. The mice reaching humane endpoints were excluded. n = 8 for vehicle group and ABT-301 (25 mg/kg) group, n = 10 for the other groups.
*$P < 0.05$, **$P < 0.01$ compared to the vehicle group by t-test.

Collectively, ABT-301 and avelumab collectively reduced the growth of CT26 tumors. The combined treatment with ABT-301 and avelumab markedly enhanced the anti-cancer effects on CT26 tumors, with ABT-301 robustly enhancing the anti-tumor growth effects of avelumab on CT26 tumors. This is evidenced by the elevated CR rate to tumor growth and the suppression of tumor volume, even at a minimal ABT-301 dosage of 25 mg/kg. These findings suggested a synergistic treatment effect, wherein a diminished quantity of ABT-301 is required to achieve a potent anti-cancer effect.

2.3 Evaluation of ABT-301 with Combination with RMP1-14

Figure 3A:
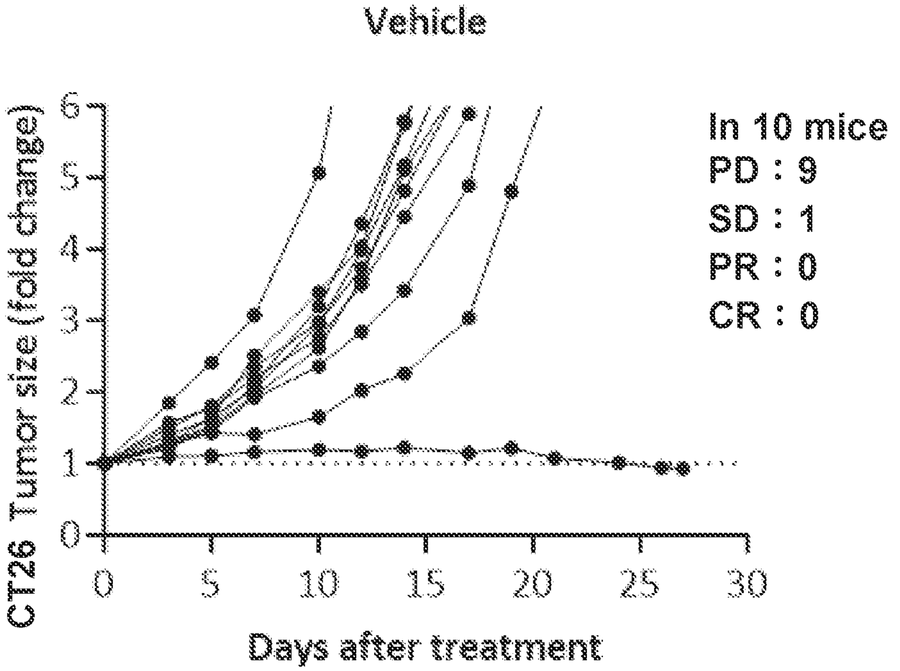
FIGS. 3A-3J are the results of treating mice bearing CT26 with a combination of ABT-301 and RMP1-14 (an anti-mouse PD-1 antibody), in which FIGS. 3A-3H respectively illustrate the number of mice exhibiting a PD, a SD, a PR, or a CR in the indicated treatment groups (n=10/group)
Figure 3B:
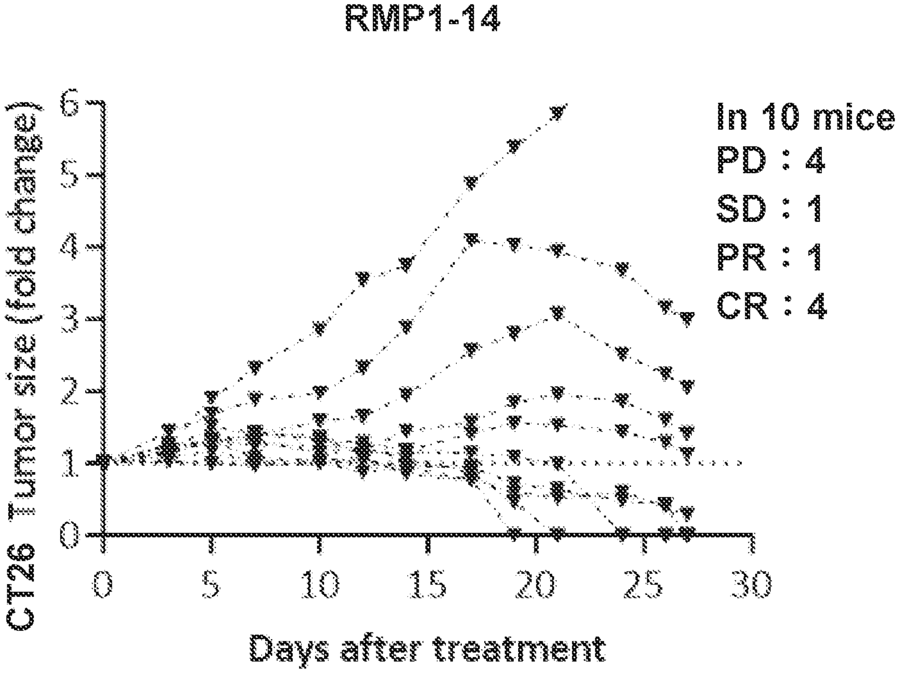
Figure 3C:
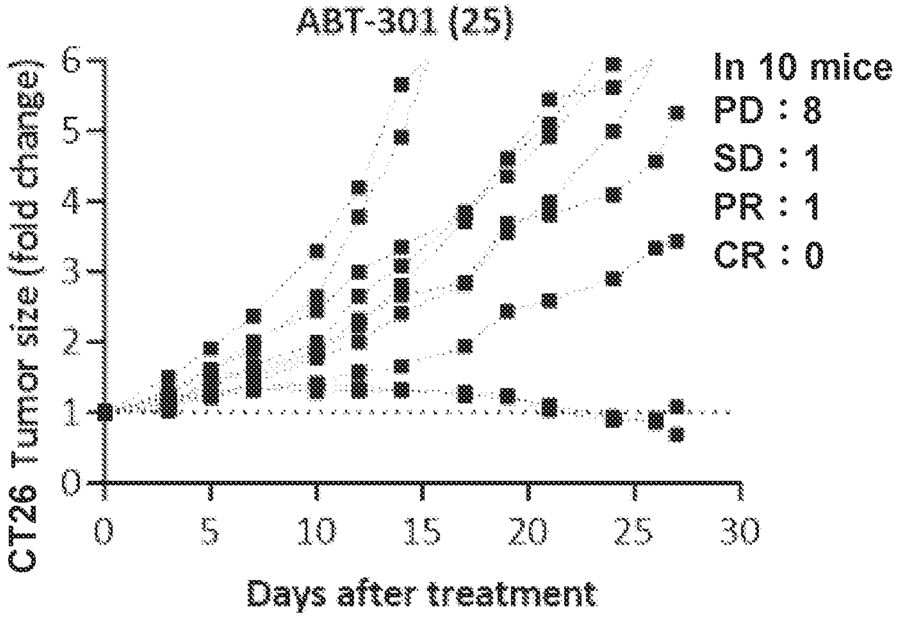
Figure 3D:
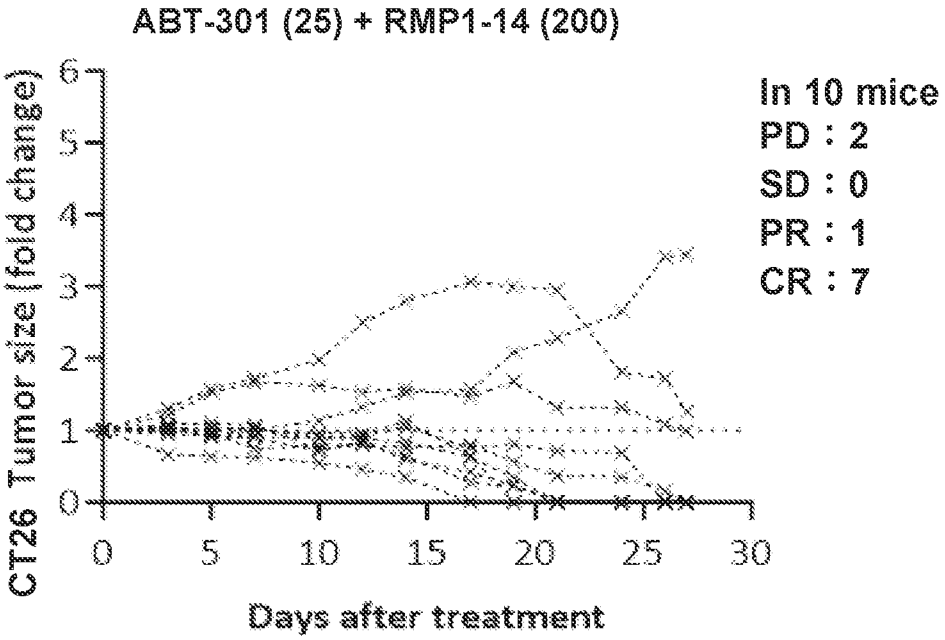
Figure 3E:
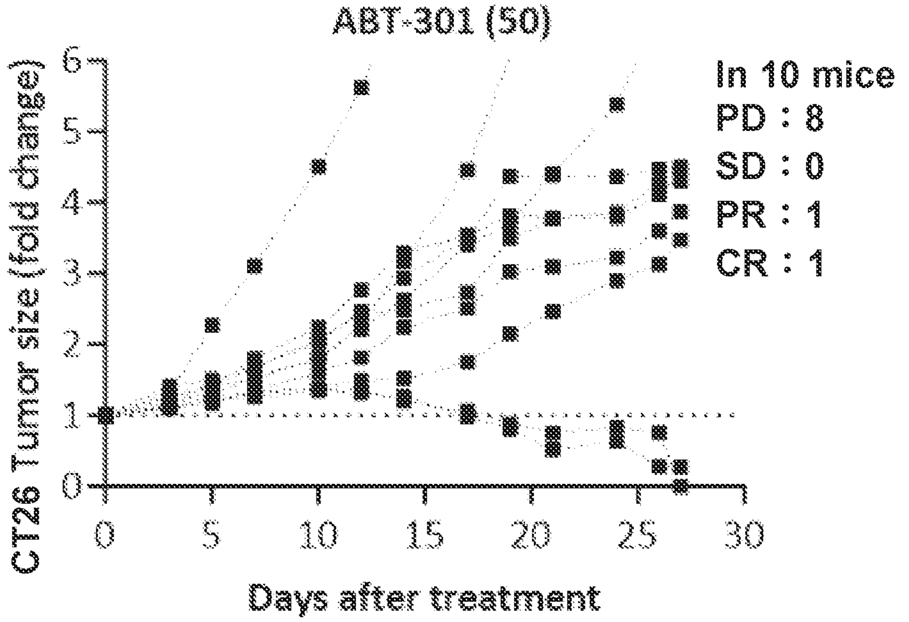
Figure 3F:
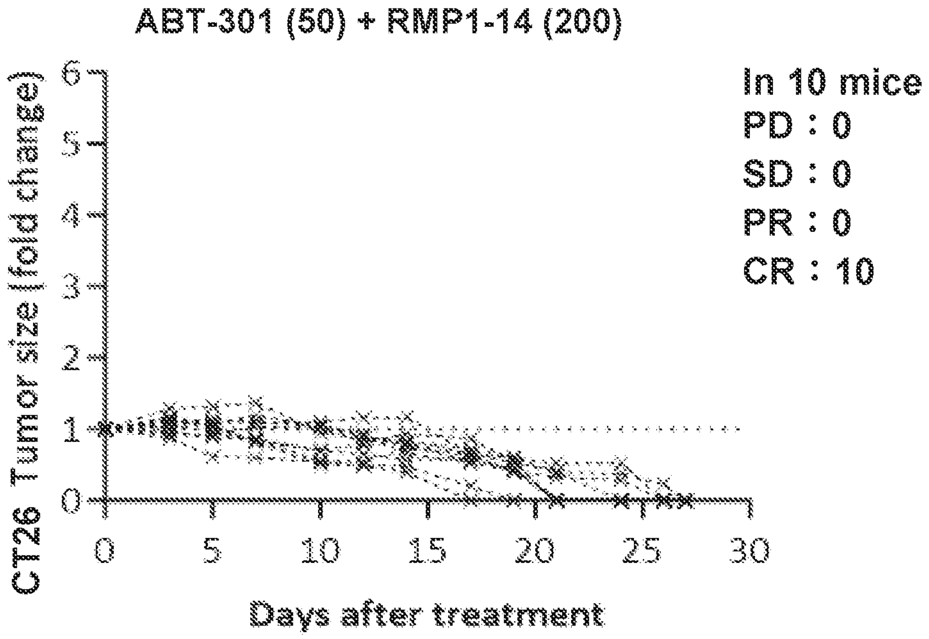
Figure 3G:
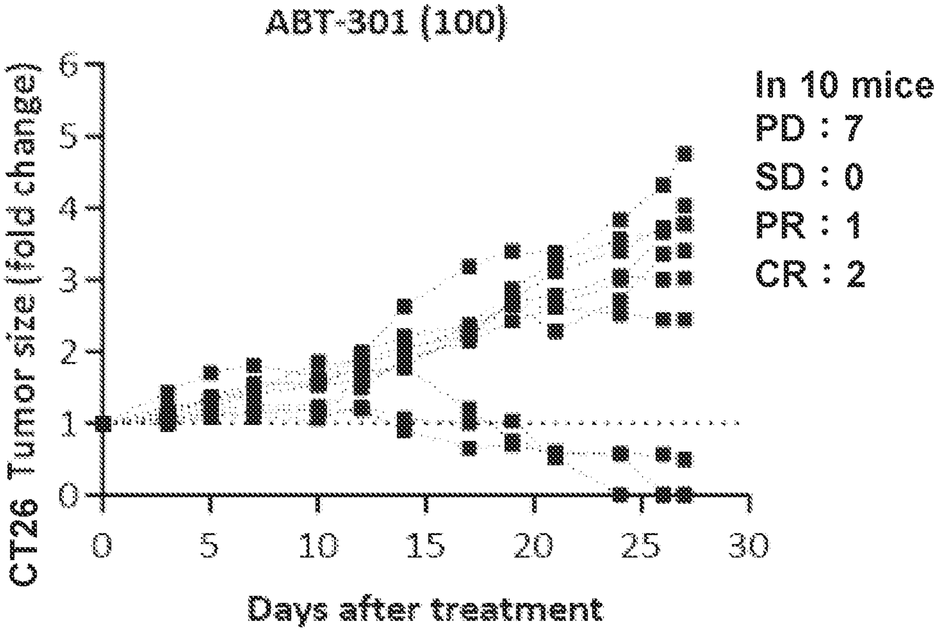
Figure 3H:
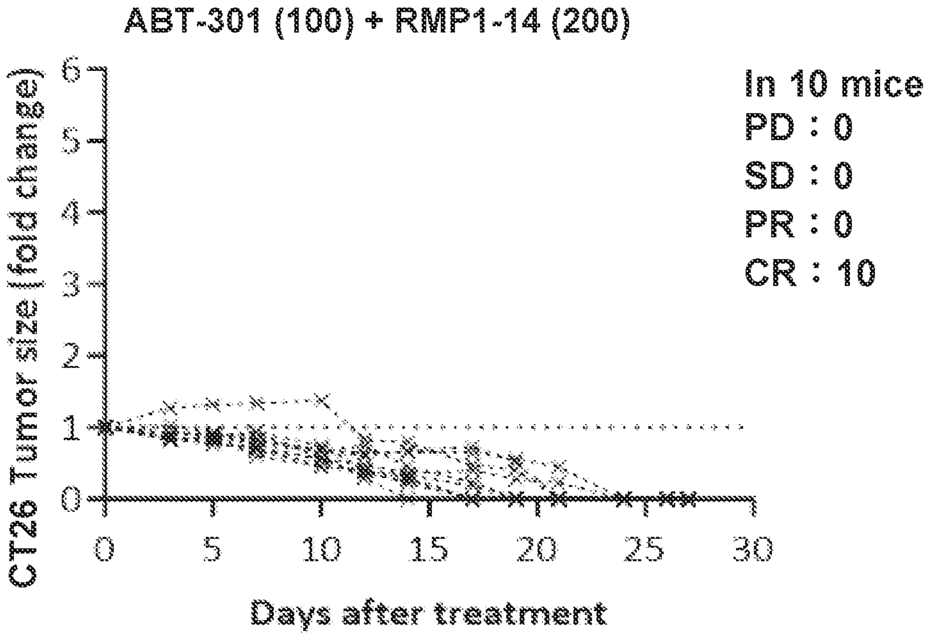
Figure 3I:
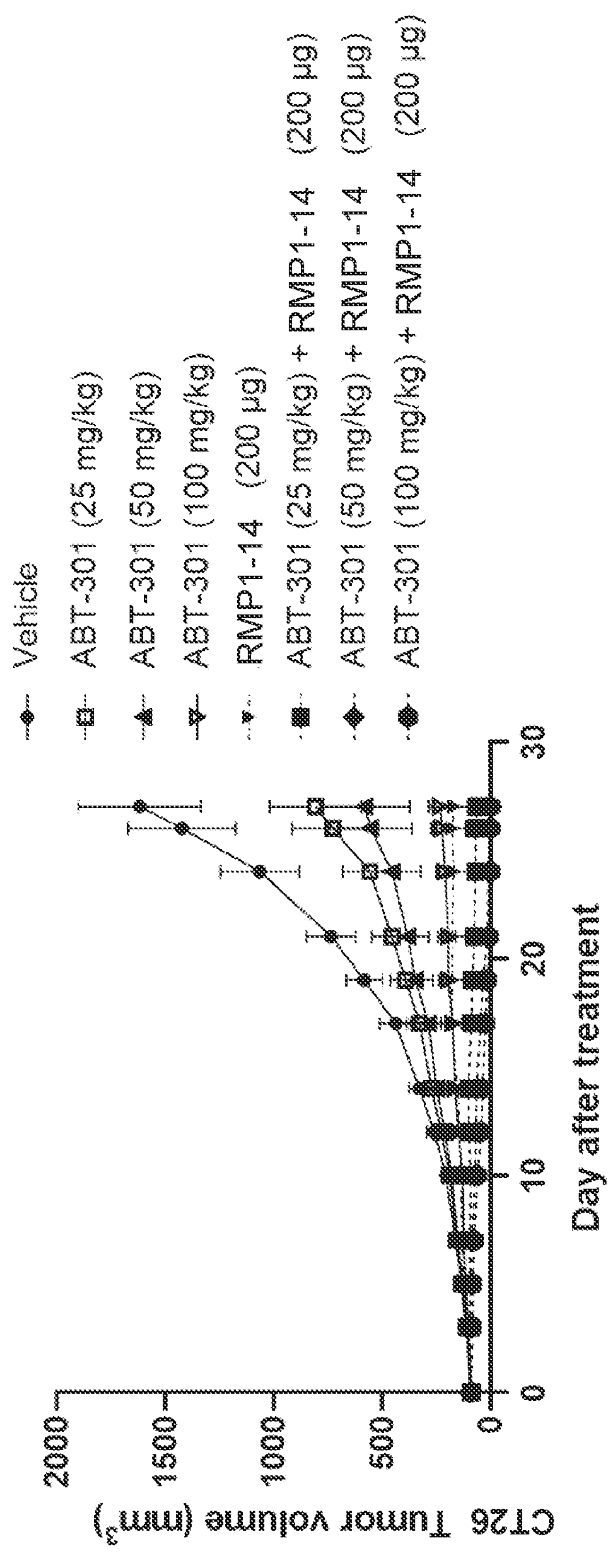

In the current example, the examination exploring the potential of ABT-301 to enhance immunotherapy in the treatment of colorectal cancer is expanded to include various dosages of ABT-301 in combination with another immune checkpoint inhibitor, specifically an anti-PD-1 antibody RMP1-14, serving as an example. The procedures were as set forth in the section of "4-3. Multiple doses of ABT-301, with or without combination with RMP1-14" of the "Materials and Methods," and the results are provided in FIGS. 3A-3J. According to FIGS. 3A-3H, analogous to the results in FIGS. 2A-2H, in contrast to the vehicle group (FIG. 3A), administration of RMP1-14 alone may yield some degree of anti-cancer activity, as indicated by the CR rate (i.e., 4 mice exhibited CR in the RMP1-14 group out of 10 mice; FIG. 3B). However, the incremental increase in ABT-301 dose from 25 mg/kg to 100 mg/kg only marginally enhanced treatment efficacy (i.e., from PD=8, SD=1, and PR=1 in the ABT-301 (25) group, to PD=7, PR=2, and CR=2 in the ABT-301 (100) group; FIGS. 3C, 3E, and 3G). Nevertheless, the combination of ABT-301 and RMP1-14 significantly enhanced the CR of the treated mice to the tumor, even at the minimal dosage of ABT-301 as low as 25 mg/kg (FIGS. 3C vs. 3D, FIGS. 3E vs. 3F, and FIGS. 3G vs. 3H). Moreover, the combination therapy yet demonstrated a dose-dependent treatment efficacy with increasing ABT-301 dosage (i.e., from PD=2, PR=1, and CR=7 in the ABT-301 (25)+RMP1-14 group, to CR=10 in the ABT-301 (100)+RMP1-14 group; FIGS. 3D, 3F, and 3H).

Figure 3J:
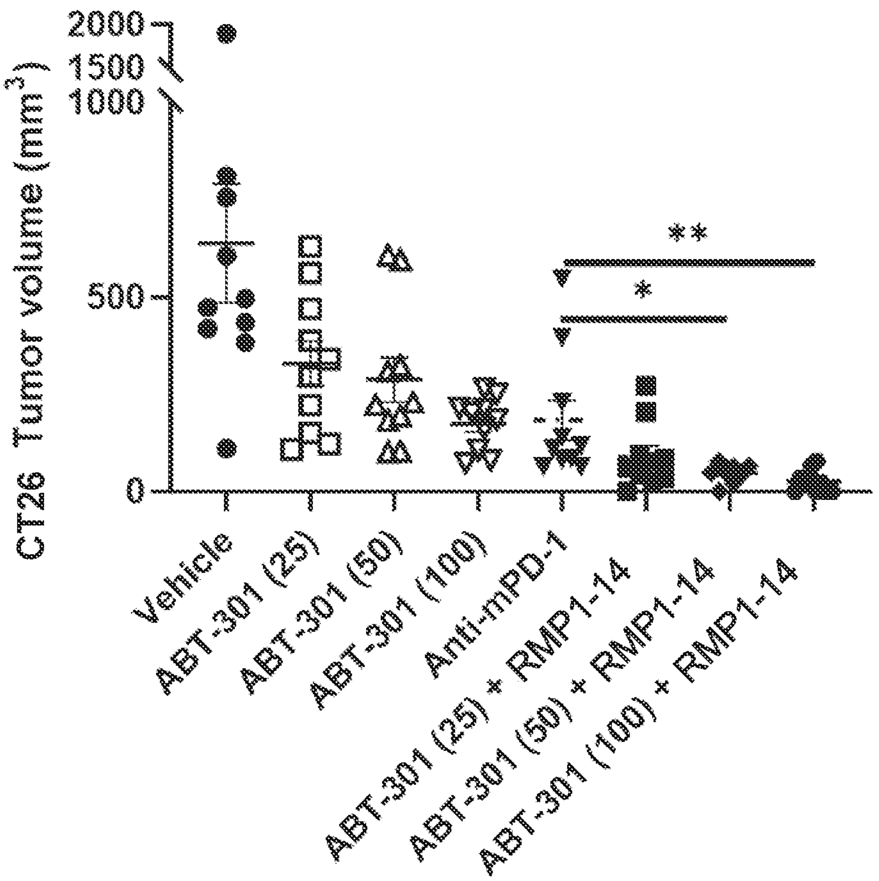

The findings pertaining to tumor volume, monitored over a span of 27 days with a specific focus on Day 17, are illustrated in FIGS. 31-3J and summarized in Table 11.

ABT-301 and RMP1-14 individually manifested distinct levels of anti-tumor activity. However, the combined therapy exhibited a pronounced suppression of tumor growth. Additionally, no statistically significant difference in body weight (%) was observed on Day 27 between each treatment group and the vehicle group (data not shown).

TABLE 11

Tumor size of CT26 allograft tumor mice following ABT-301 and RMP1-14 treatments on Day 27

| Groups | Day 27 after treatments Tumor size ($mm^3$) |
|---|---|
| Vehicle | 1619.28 ± 283.33 |
| RMP1-14 (200 μg) | 169.43 ± 95.65*** |
| ABT-301 (25 mg/kg) | 806.83 ± 212.06* |
| ABT-301 (25 mg/kg) + RMP1-14 (200 μg) | 62.69 ± 44.90*** |
| ABT-301 (50 mg/kg) | 580.33 ± 206.53** |
| ABT-301 (50 mg/kg) + RMP1-14 (200 μg) | 0 ± 0*** |
| ABT-301 (100 mg/kg) | 234.59 ± 52.38** |
| ABT-301 (100 mg/kg) + RMP1-14 (200 μg) | 0 ± 0*** |

The data are presented as means ± SEM. The dead mice and mice reaching humane endpoints were excluded. n = 7 for vehicle group, n = 10 for the other groups.
*P < 0.05, P < 0.01, *P < 0.001 compared to the vehicle group by one-way ANOVA followed by Tukey's multiple comparisons test by t-test.

Taken together, ABT-301 and RMP1-14 collectively attenuated the growth of CT26 tumors. The combined treatment with ABT-301 and RMP1-14 significantly augmented the anti-cancer effects on CT26 tumors, with ABT-301 continuing to robustly enhance the anti-tumor growth effects of RMP1-14 on CT26 tumors. This is substantiated by the elevated CR rate to tumor growth and the suppression of tumor volume, even at a minimal ABT-301 dosage of 25 mg/kg. These findings suggest a synergistic treatment effect existed when ABT-301 was administered in combination with RMP1-14, wherein a potent anti-cancer effect may be achieved with a reduced amount of ABT-301.

Example 3 Effects of ABT-301 on the Inhibition of MSI-H Subtype Colorectal Cancer

3.1 Evaluation of ABT-301 with Combination with Avelumab or RMP1-14

To investigate the efficacy of ABT-301 in treating MSI-H subtype colorectal cancer and its potential to enhance the effectiveness of immunotherapy against MSI-H subtype colorectal cancer, the ensuing experiments were undertaken.

Figure 4A:
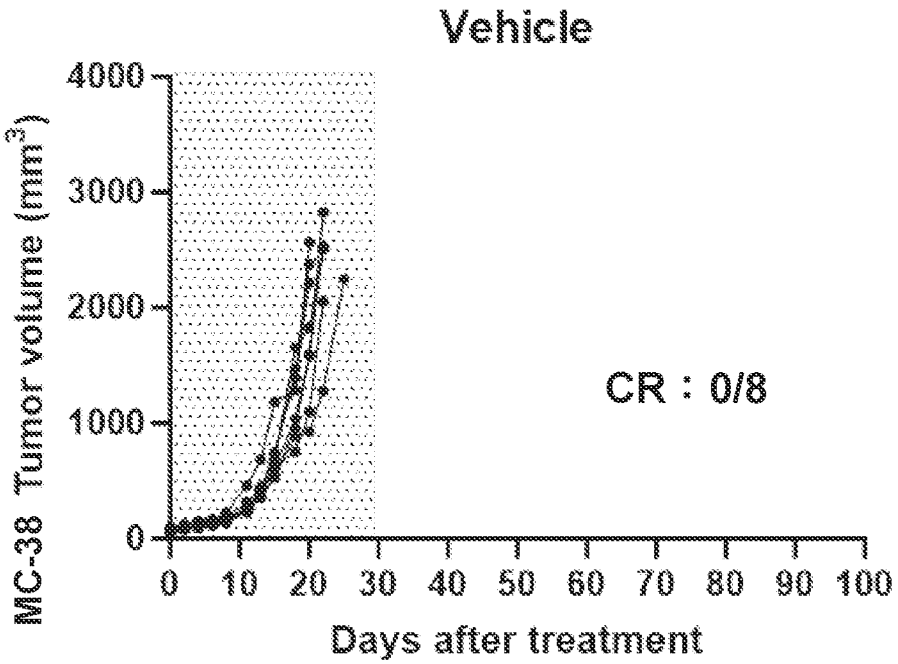
FIGS. 4A-4I are the results of treating mice bearing MC-38 (a microsatellite instable-high (MSI-H) subtype colorectal carcinoma cell line) with a combination ofABT-301 and avelumab or RMP1-14, in which FIGS. 4A-4F respectively illustrate the number of mice exhibiting a complete response (CR) in the indicated treatment groups (n=8/group)
Figure 4B:
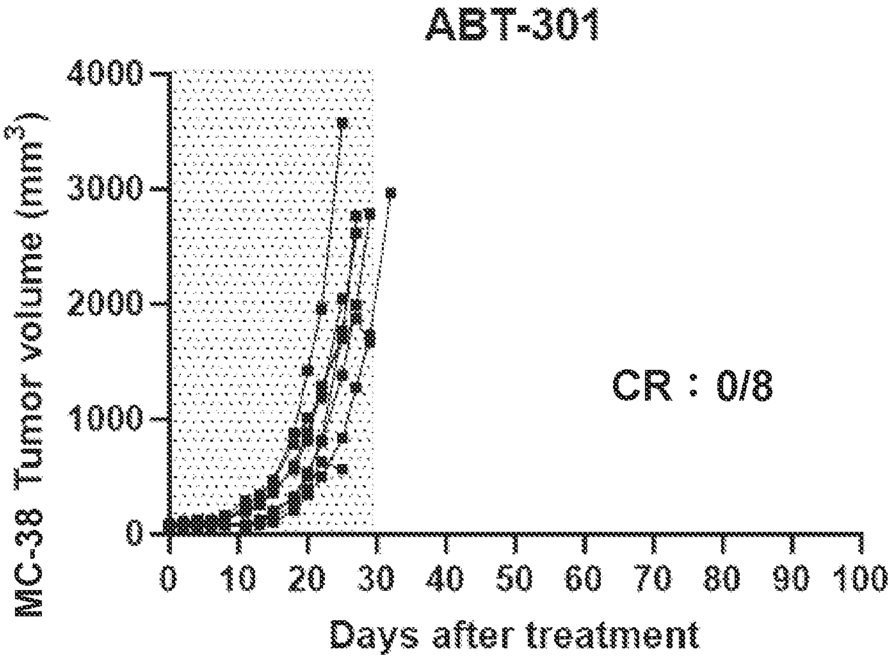

The study was conducted in accordance with the procedures detailed in the section of "5-1. A single dose of ABT-301, with or without combination with avelumab or RMP1-14" of the "Materials and Methods." Immunotherapy was executed by administering avelumab or RMP1-14 to the mice, and the results are illustrated in FIGS. 4A-4I. Tumor growth results in MC-38-bearing mice are presented in FIGS. 4A-4F, focusing on depicting the CR for the indicated treatments against tumor growth in the treated mice. According to the results, compared to the vehicle group, administering ABT-301 alone did not significantly increase the number of mice exhibiting CR to the tumor (i.e., the CR rates for the vehicle and ABT-301 groups were both 0/8; FIGS. 4A-4B). According to the literature, immune checkpoint inhibitors exhibit high response and survival rates for treating MSI-H subtype colorectal cancer compared to MSS subtype tumors, thereby resulting in higher survival rates.

Figure 4C:
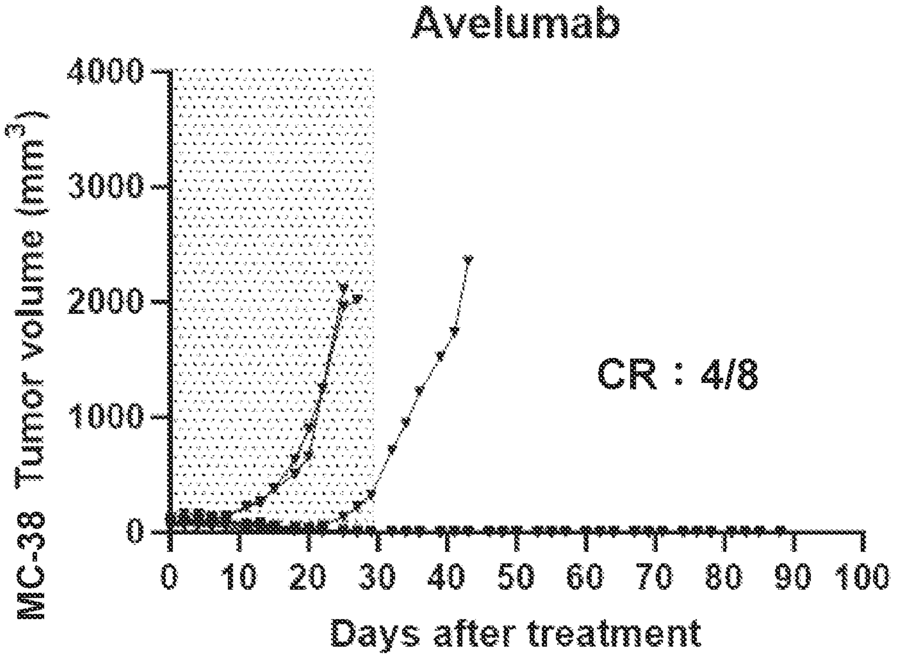
Figure 4D:
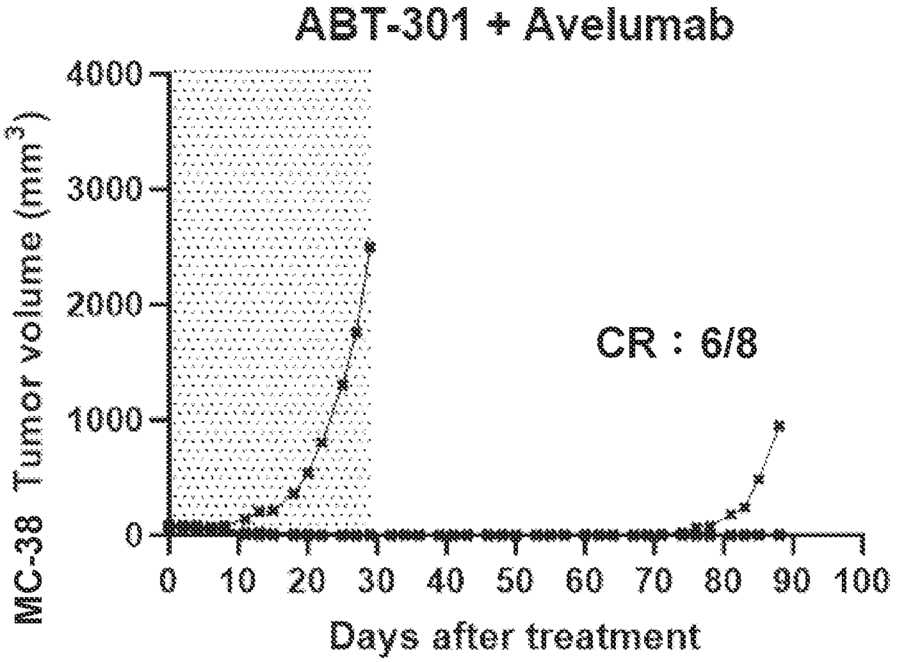
Figure 4E:
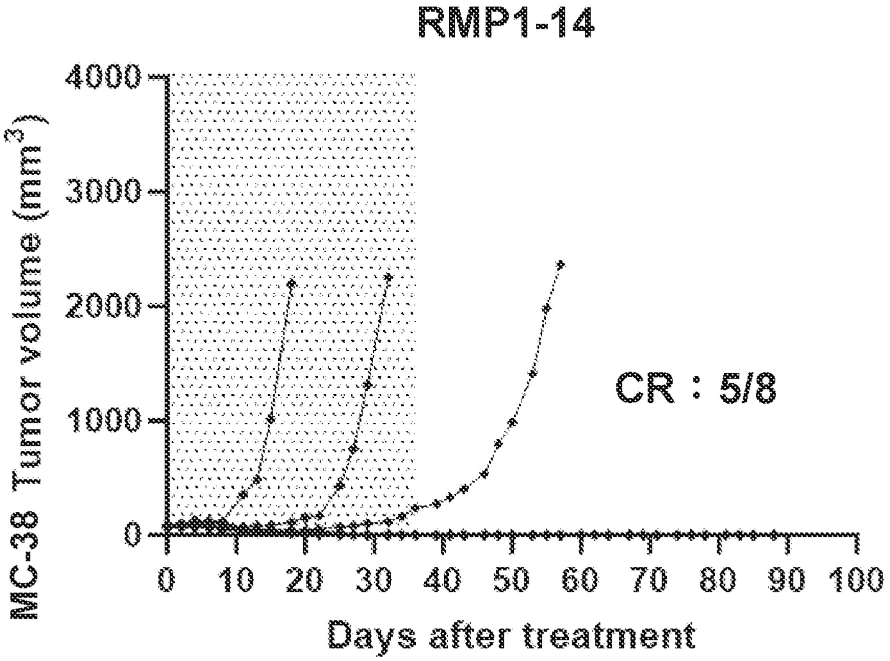
Figure 4F:
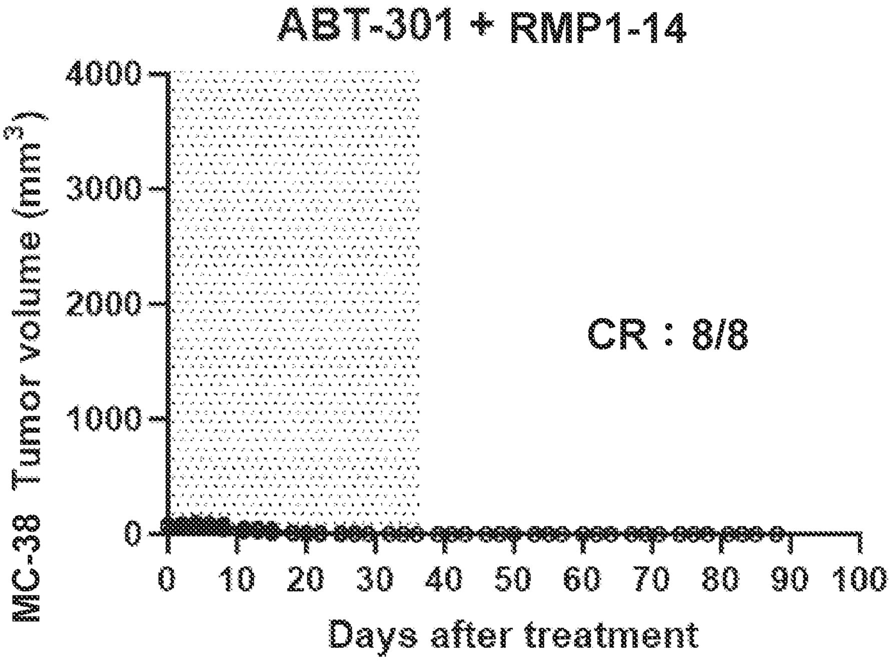

Similarly, it was observed that administering avelumab or RMP1-14 alone achieved some extent of anti-cancer effect (the CR rates for the avelumab and RMP1-14 groups were 4/8 and 5/8, respectively; FIGS. 4C and 4E). However, under such circumstances, ABT-301 could still further enhance the efficacy of avelumab or RMP1-14 in treating MSI-H subtype colorectal cancer when combined with avelumab or RMP1-14; the combined administration of ABT-301 and avelumab or RMP1-14 significantly increased the CR rate in the treated mice (the CR rates for the ABT-301+avelumab and ABT-301+RMP1-14 groups were 6/8 and 8/8, respectively; FIGS. 4D and 4F).

Figure 4G:
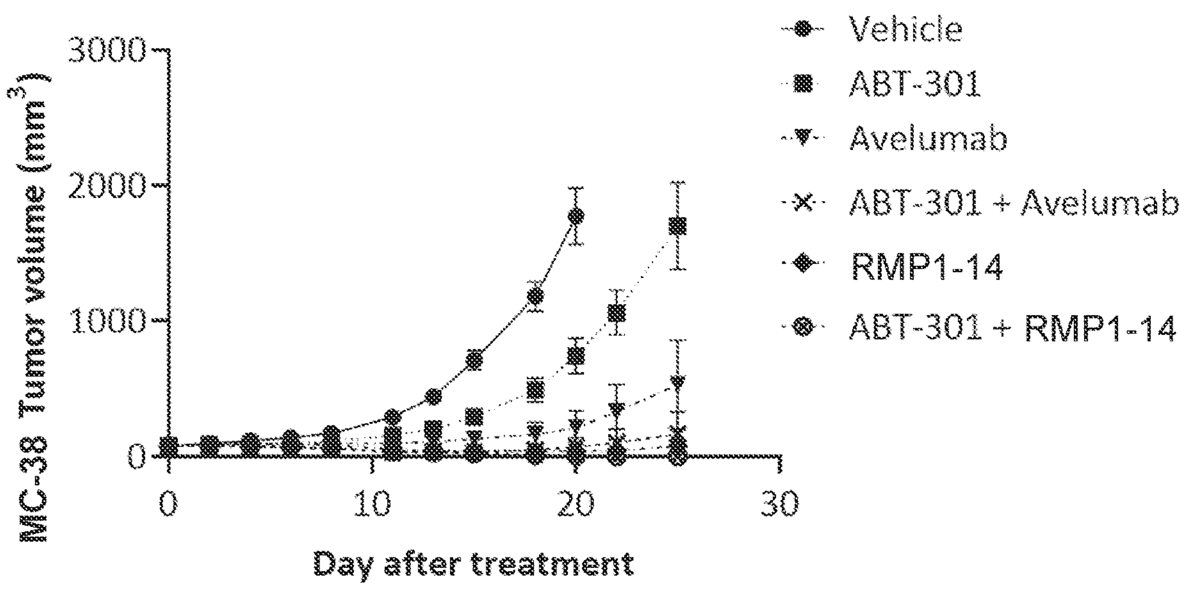
Figure 4H:
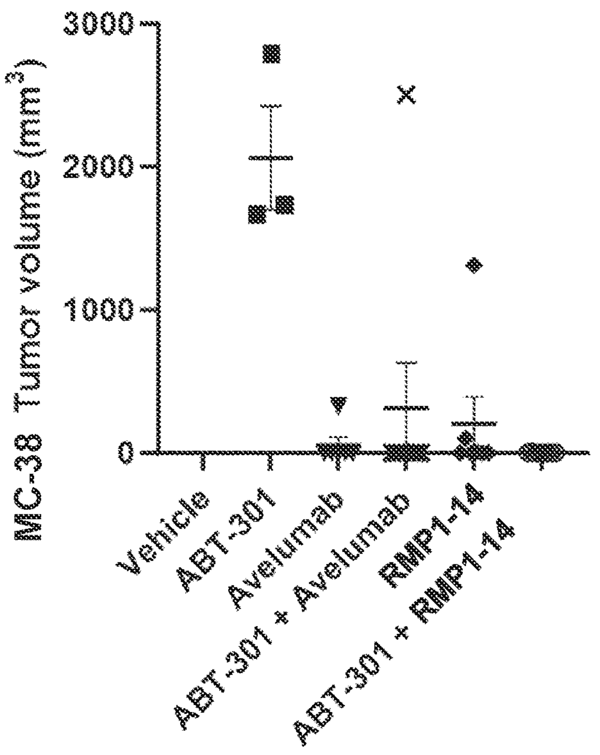

The findings regarding tumor volume recorded over a period of 25 days, with a specific focus on Day 25, are illustrated in FIGS. 4G-4H and summarized in Table 12. ABT-301, avelumab, and RMP1-14 individually manifested varying levels of anti-tumor activity. However, the combined therapy demonstrated more potent suppression of tumor growth. The mice in the vehicle group were sacrificed on Day 20 due to reaching the humane endpoints. Additionally, no statistically significant difference in body weight (%) was observed on Day 25 between each treatment group and the vehicle group (data not shown).

TABLE 12

Tumor size of MC-38 allograft tumor mice following ABT-301 and avelumab or RMP1-14 treatments on Day 25

| Groups | Day 25 after treatments Tumor size ($mm^3$) |
|---|---|
| Vehicle | 2248.07 |
| ABT-301 (100 mg/kg, PO) | 1701.49 ± 321.46 |
| Avelumab (200 μg, IP) | 529.91 ± 329.24 |
| ABT-301 (100 mg/kg, PO) + Avelumab (200 μg, IP) | 163.05 ± 163.05 |
| RMP1-14 (200 μg, IP) | 76.28 ± 60.11 |
| ABT-301 (100 mg/kg, PO) + RMP1-14 (200 μg, IP) | 2.47 ± 2.47 |

The data are presented as means ± SEM. The dead mice and mice reaching humane endpoints were excluded. n = 1 for vehicle group, n = 8 for ABT-301 group, n = 8 for Avelumab group, n = 8 for ABT-301 + Avelumab group, n = 7 for RMP1-14 group, n = 8 for Avelumab group and n = 8 for ABT-301 + RMP1-14 group.

Figure 4I:
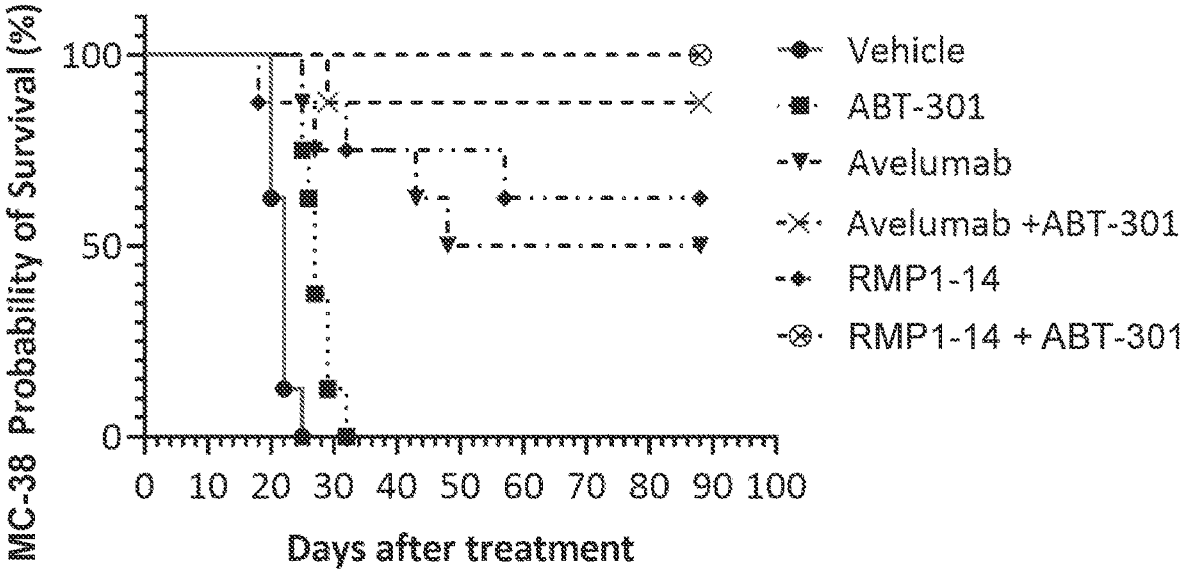

Additionally, although the mice in the avelumab or RMP1-14 treatment groups exhibited considerable survival rates compared to the mice in the vehicle group, the combined therapy (either ABT-301+avelumab or ABT-301+RMP1-14) substantially increased the survival rate of the treated mice (FIG. 4I and Table 13). Taken together, while avelumab or RMP1-14 alone may demonstrate anti-cancer activity, the combination of ABT-301 with avelumab or RMP1-14 could robustly enhance the anti-tumor growth effects of avelumab or RMP1-14 on MC-38 tumors, as evidenced by the CR to tumor growth and the suppression of tumor volume. Moreover, the combined treatment of ABT-301 and avelumab or RMP1-14 could prolong the survival of MC-38-bearing mice compared to avelumab or RMP1-14 treatment alone.

TABLE 13

Median survival of MC-38 allograft tumor mice following ABT-301 and Avelumab or RMP1-14 treatments over the entire study

| (Day) | Vehicle | ABT-301 | Avelumab | ABT-301 + Avelumab | RMP1-14 | ABT-301 + RMP1-14 |
|---|---|---|---|---|---|---|
| Median survival | 22 | 27 | 68 | >88 | >88 | >88 |

Figure 5A:
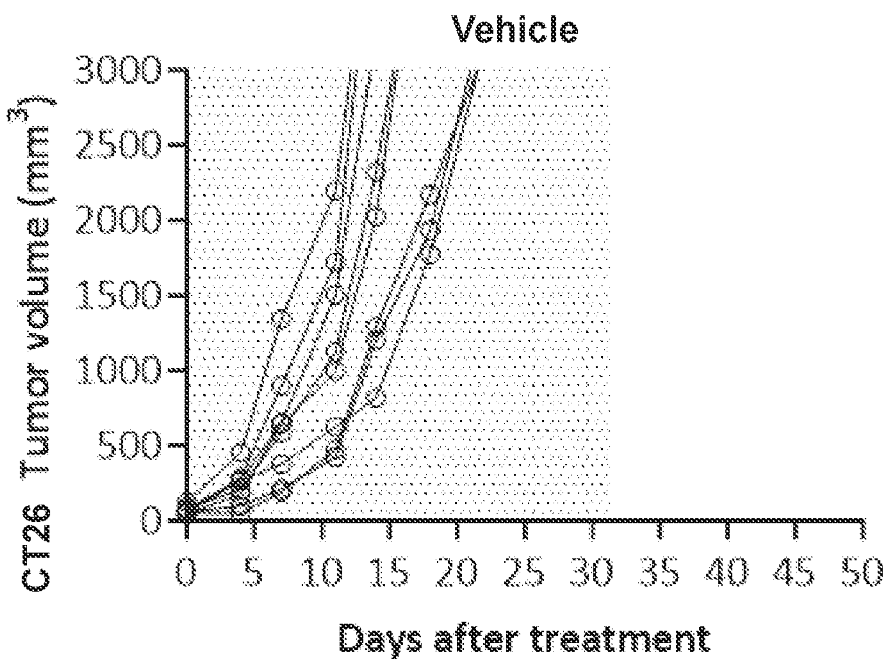
FIGS. 5A-5K are the results of treating mice bearing CT26 with a combination of a HDAC inhibitor (ABT-301, vorinostat, or citarinostat) and RMP1-14, in which FIGS. 5A-5H respectively illustrate the tumor volume of each mice in the indicated treatment groups (n=8 or 9/group)
Figure 5B:
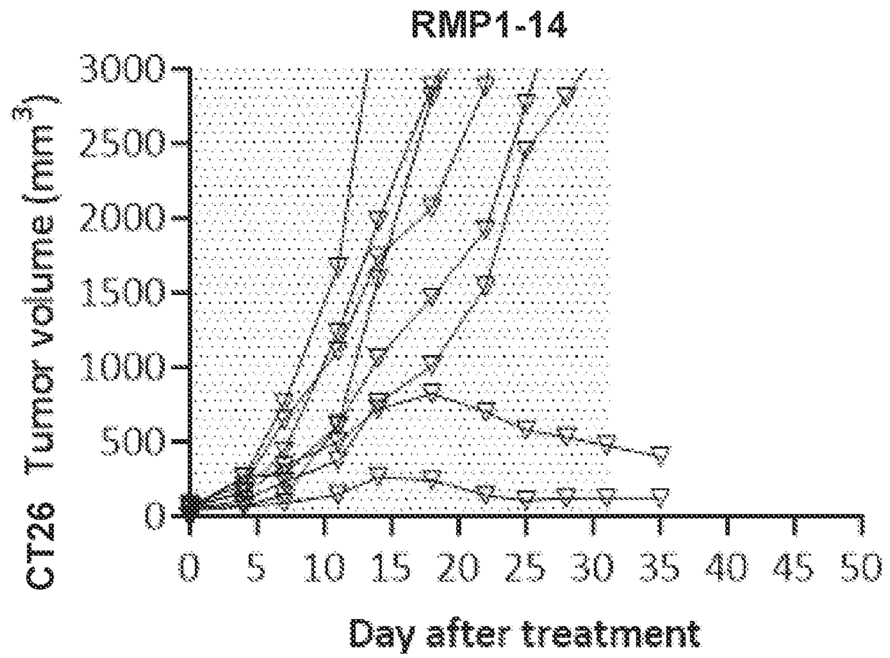
Figure 5C:
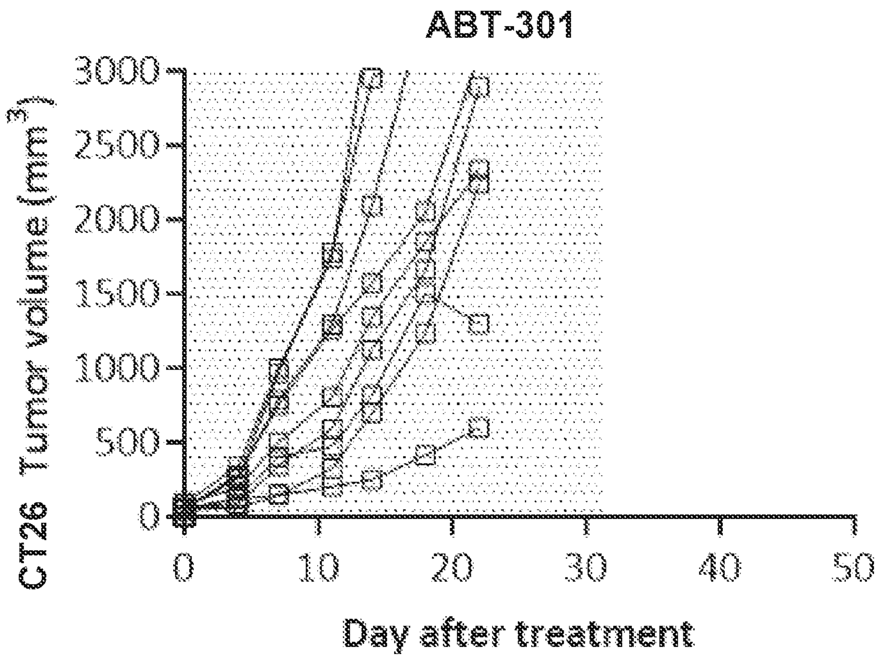
Figure 5D:
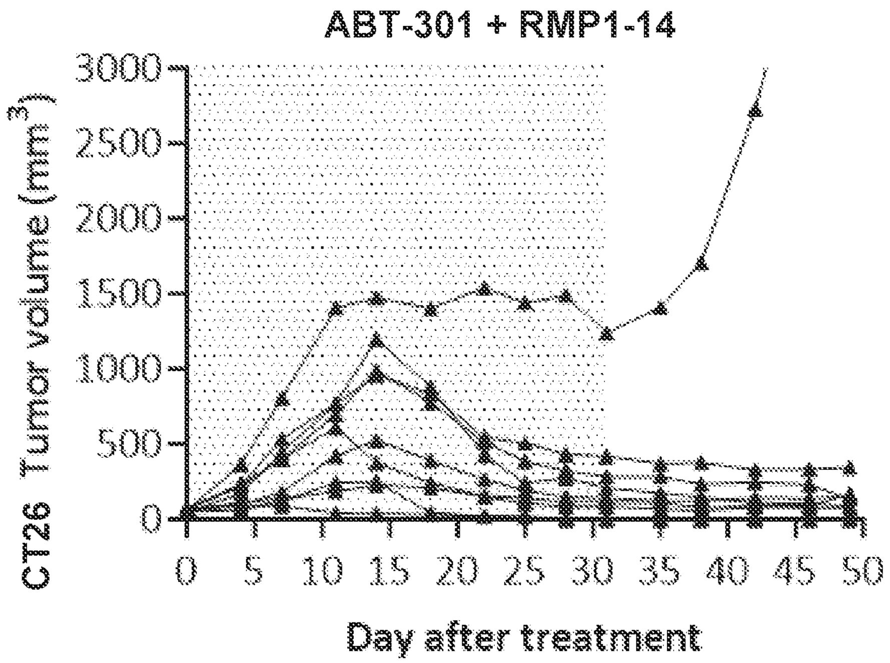
Figure 5E:
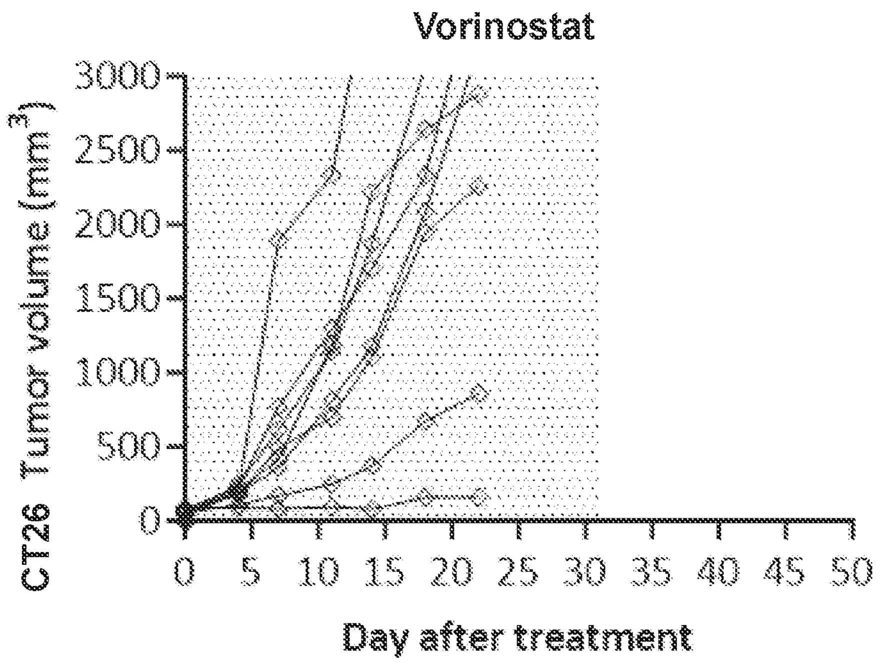
Figure 5F:
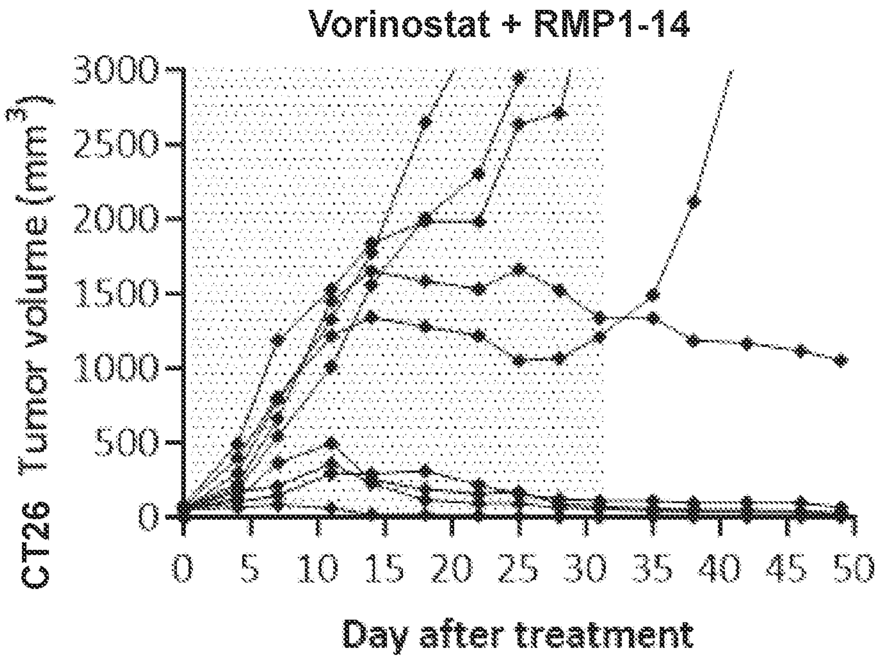
Figure 5G:
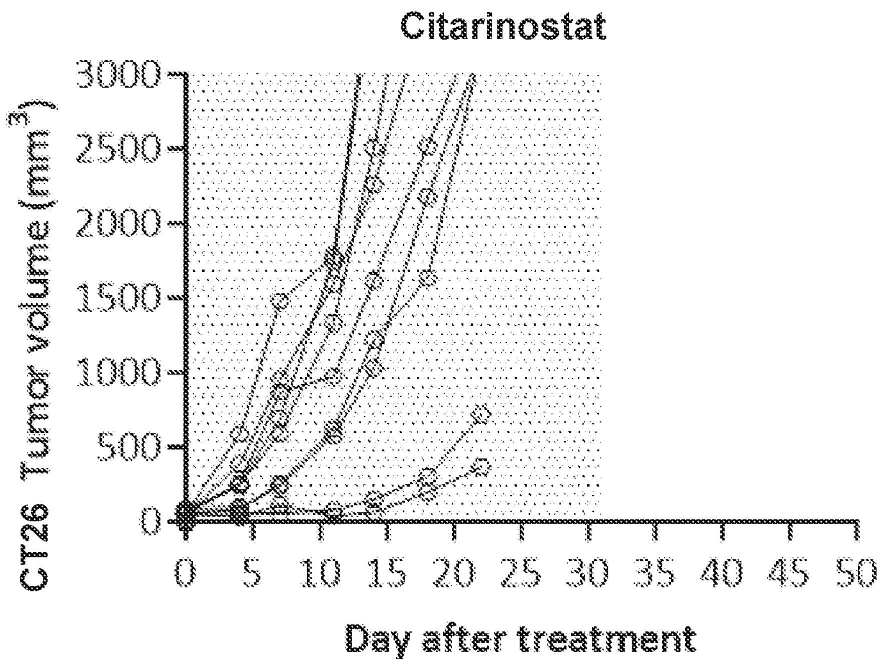
Figure 5H:
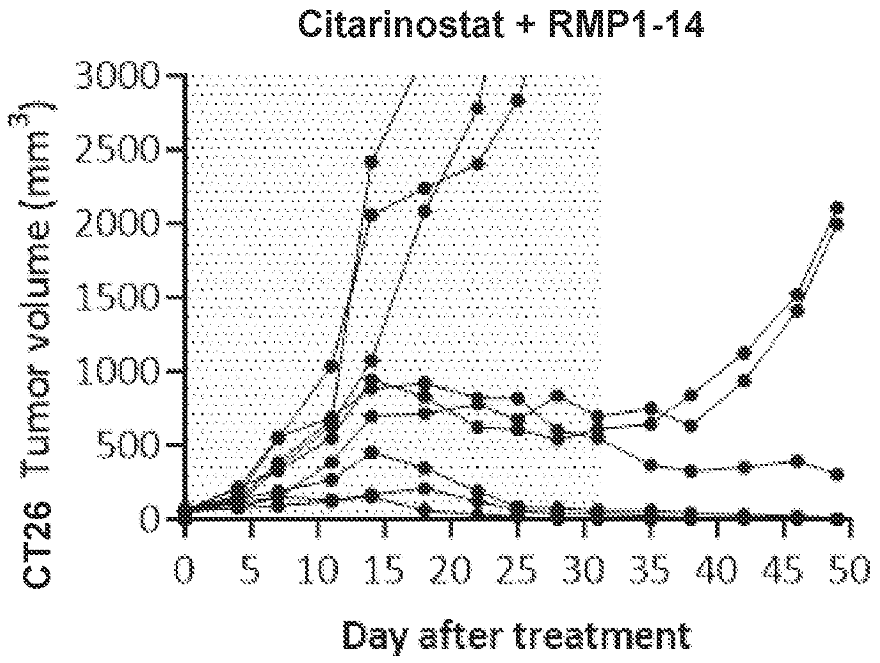

Example 4 Effects of HDAC Inhibitors in Combination with RMP1-14 on the Growth of Colorectal Cancer The present example aimed at assessing the efficacy of combined treatment of different HDAC inhibitors and RMP1-14 on colorectal cancer. To this end, different HDAC inhibitors, including ABT-301 (a pan-HDAC inhibitor), vorinostat (a pan-HDAC inhibitor), and citarinostat (a type-specific HDAC inhibitor targeting HDAC6), were co-administered with RMP1-14 to test animals in the present study. The procedures for conducting the study were detailed in the section of "4-4. HDAC inhibitors, with or without combination with RMP1-14" of this paper, and the results are illustrated in FIGS. 5A-5K. Tumor growth results in CT26-bearing mice are presented in FIGS. 5A-5H. As compared to the vehicle group, the administration of RMP1-14 alone or HDAC inhibitors alone, namely ABT-301, vorinostat, or citarinostat alone, did not elicit a visible response in the mice on the growth of tumor (FIGS. 5A-5C, 5E, and 5G). Nevertheless, the co-administration of HDAC inhibitors with RMP1-14 elicited varying degrees of response in the mice, particularly toward the volume of the colorectal cancer. According to the results, the co-administration of ABT-301 with RMP1-14 exhibited better responses to tumors compared to the co-administration of vorinostat and RMP1-14 or the co-administration of citarinostat and RMP1-14 (FIGS. 5D, 5F, and 5H).

In another batch of experiments, it was also found that the administration of RMP1-14 alone or other HDAC inhibitors alone, namely ABT-301, PCI-34051 (a type-specific HDAC inhibitor targeting HDAC8), or elevenostat (a type-specific HDAC inhibitor targeting HDAC11) alone, did not elicit a visible response in the mice on the growth of tumor as compared to the vehicle group; conversely, the co-administration of ABT-301 with RMP1-14 exhibited better responses to tumors compared to the co-administration of PCI-34051 and RMP1-14 or the co-administration of elevenostat and RMP1-14 (data not shown).

Figure 5I:
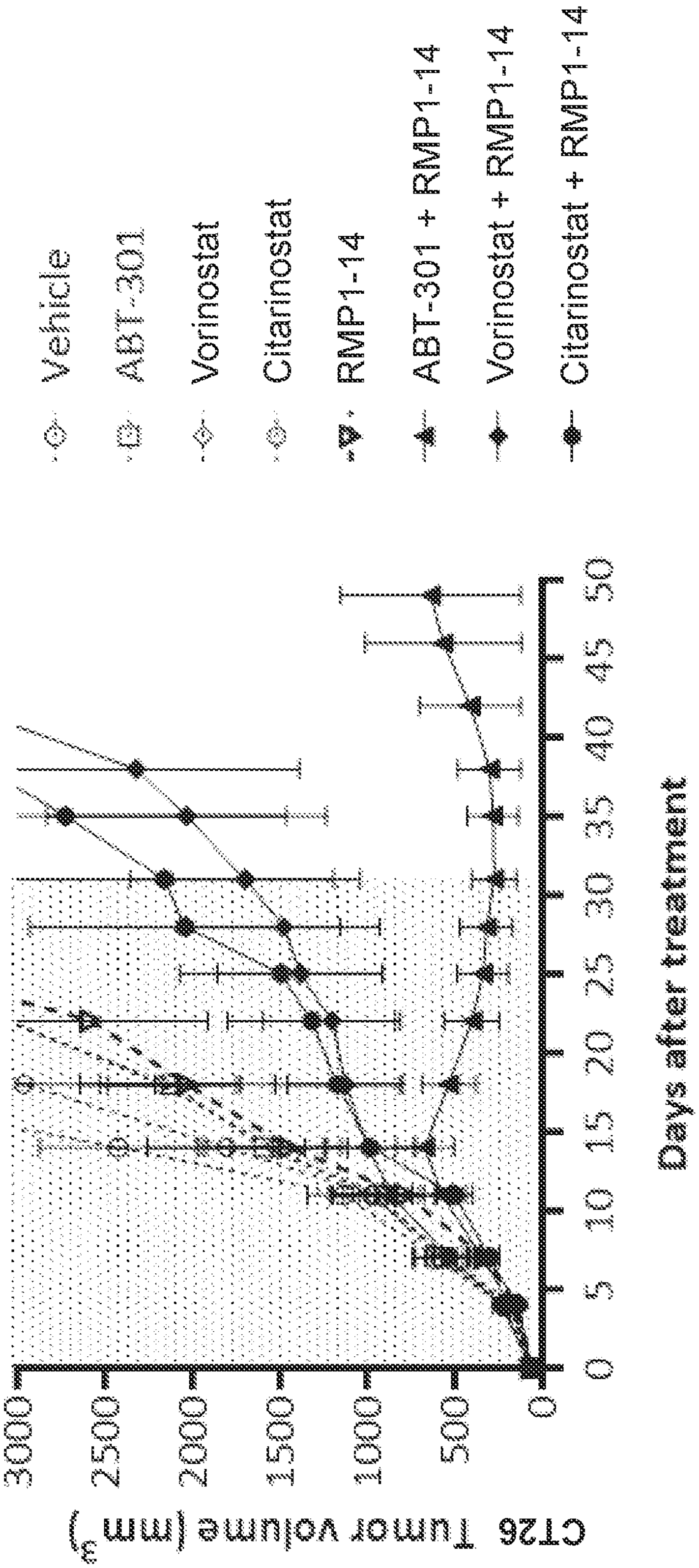
Figure 5J:
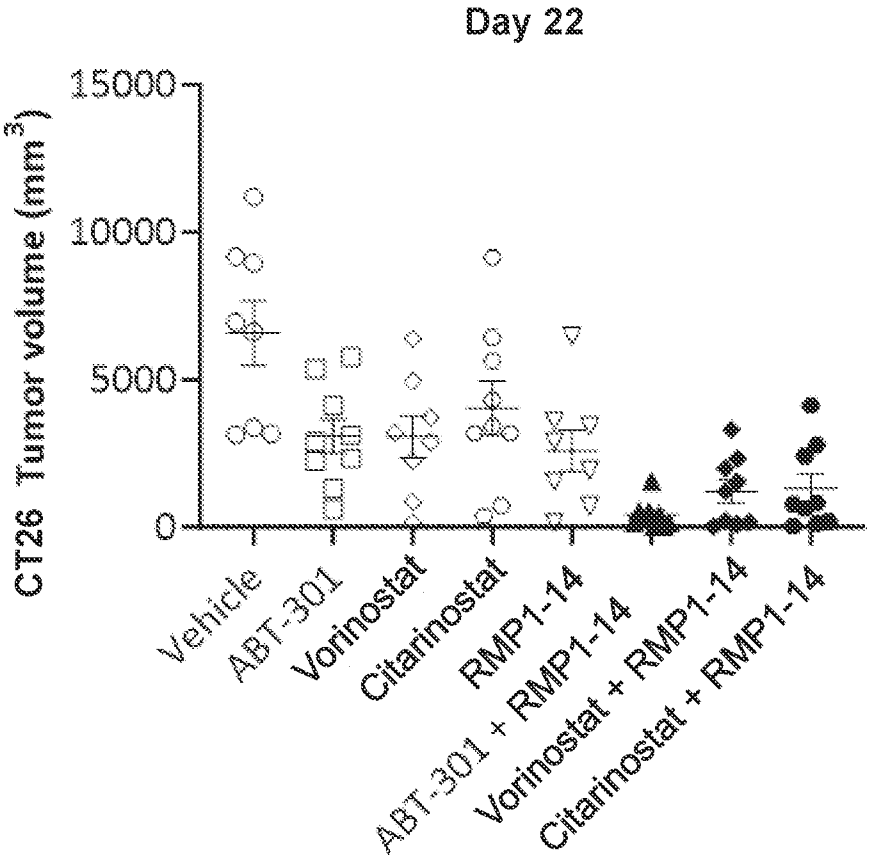
Figure 5K:
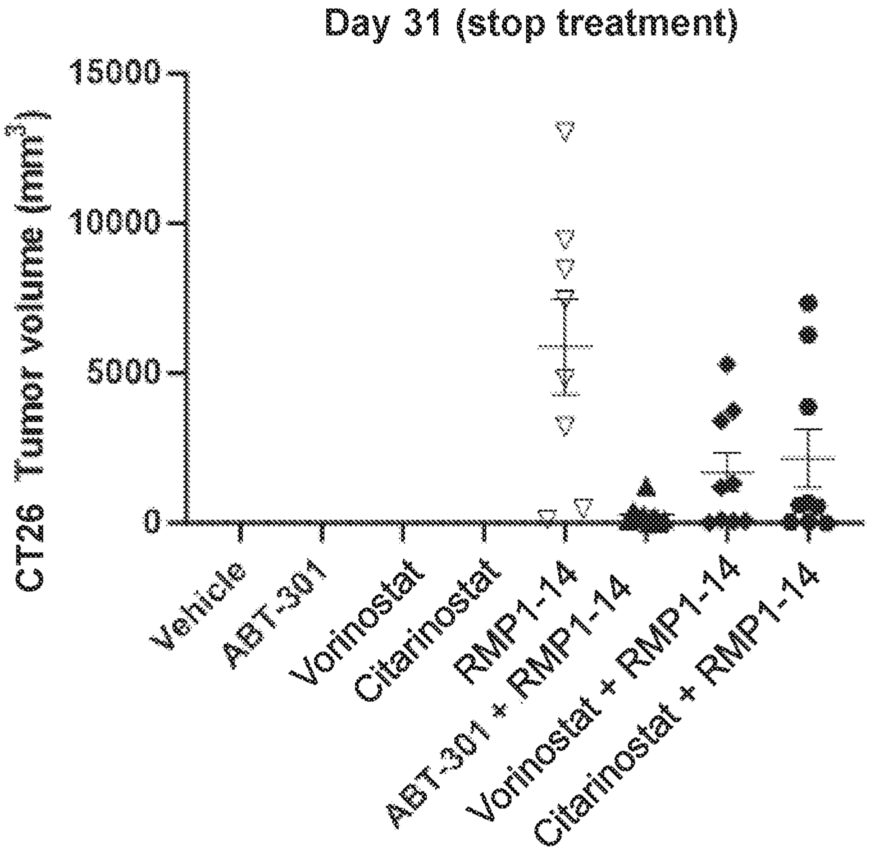

The changes in tumor volume were recorded over a period of 49 days, with a specific focus on Day 22 and Day 31, see FIGS. 5I-5K and Table 14. The mice treated with the combination of ABT-301 and RMP1-14 had the smallest tumor volumes among all experimental groups (FIG. 5I). On Day 22, individual administrations of ABT-301, vorinostat, citarinostat, or RMP1-14 showed varying degrees of anti-tumor activity. However, the combined therapy exhibited a more robust suppression of tumor growth, with the combination of ABT-301 and RMP1-14 exhibiting the most evident suppression ability (FIG. 5J and Table 14). The mice in the vehicle, the ABT-301, the vorinostat, and the citarinostat groups were then sacrificed, as they had reached the humane endpoints. On Day 31, after the treatment was terminated, mice treated with the combination of ABT-301 and RMP1-14 still exhibited the smallest tumor volumes among all experimental groups. This finding indicates that the combined therapy (ABT-301 and RMP1-14) can persistently and effectively suppress tumor growth, in contrast to other combination therapies that exhibited tumor regrowth (FIG. 5K). Additionally, no statistically significant difference in body weight (%) was observed during the entire experiment period between each treatment group and the vehicle group (data not shown).

TABLE 14

Tumor growth inhibition of CT26 allograft tumor mice following HDAC inhibitors and RMP1-14 treatments on Day 22

| Groups | Day 22 after treatments TGI (%) |
|---|---|
| Vehicle | — |
| RMP1-14 (200 μg) | 61 |
| ABT-301 (100 mg/kg) | 53.5 |
| ABT-301 (100 mg/kg) + RMP1-14 (200 μg) | 94.7 |
| Vorinostat (100 mg/kg) | 54 |
| Vorinostat (100 mg/kg) + RMP1-14 (200 μg) | 82.4 |
| Citarinostat (50 mg/kg) | 38 |
| Citarinostat (50 mg/kg) + RMP1-14 (200 μg) | 80.6 |

Collectively, these data suggest that the combination of a pan-HDAC inhibitor with an anti-PD-1 antibody (e.g., RMP1-14) exhibits superior anti-cancer activity compared to the combination of a type-specific HDAC inhibitor (e.g., citarinostat, PCI-34051, or elevenostat) with an anti-PD-1 antibody. However, within the combinations having a pan-HDAC inhibitor and an anti-PD-1 antibody, the combination ofABT-301 and RMP1-14 could enhance anti-cancer activity in comparison to the combination with the other pan-HDAC inhibitor (e.g., vorinostat) and RMP1-14.

In conclusion, the present invention provides an improved therapeutic approach for the treatment of colorectal cancer, including both MSS and MSI-H subtypes, by employing the agent ABT-301 in combination with an anti-PD-1 or anti-PD-L1 antibody. The combined therapy demonstrates improved therapeutic efficacy, thereby alleviating the burden on patients affected by the disease.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

SEQUENCE LISTING

```
Sequence total quantity: 2
SEQ ID NO: 1            moltype = AA  length = 4
FEATURE                 Location/Qualifiers
source                  1..4
                        mol_type = protein
                        organism = synthetic construct
MOD_RES                 4
                        note = C-acetyllysine and 7-amino-4-methyl coumarin (AMC)
SEQUENCE: 1
RHKK                                                                  4

SEQ ID NO: 2            moltype = AA  length = 4
FEATURE                 Location/Qualifiers
source                  1..4
                        mol_type = protein
                        organism = synthetic construct
MOD_RES                 3
                        note = C-acetyllysine
MOD_RES                 4
                        note = C-acetyllysine and 7-amino-4-methyl coumarin (AMC)
SEQUENCE: 2
RHKK                                                                  4
```

What is claimed is:

1. A pharmaceutical kit for treating colorectal cancer in a subject, comprising a first container containing (E)-N-hydroxy-3-(1-(phenylsulfonyl)-indolin-5-yl)-acrylamide; and a second container containing an anti-PD-1 or anti-PD-L1 antibody.

2. The pharmaceutical kit of claim 1, wherein the anti-PD-1 antibody is selected from the group consisting of cemiplimab, pembrolizumab, nivolumab, and RMP1-14.

3. The pharmaceutical kit of claim 1, wherein the anti-PD-L1 antibody is selected from the group consisting of atezolizumab, avelumab, and durvalumab.

4. The pharmaceutical kit of claim 1, wherein the colorectal cancer is a microsatellite stable-type or microsatellite instable-type colorectal cancer.

5. A method for treating colorectal cancer in a subject, comprising administering to the subject the pharmaceutical kit of claim 1, wherein the (E)-N-hydroxy-3-(1-(phenylsulfonyl)-indolin-5-yl)-acrylamide is administered to the subject in the amount of about 10 μg/kg-1 g/kg; and the anti-PD-1 or anti-PD-L1 antibody is administered to the subject in the amount of about 1 μg/kg-100 mg/kg.

6. The method of claim 5, wherein the anti-PD-1 antibody is selected from the group consisting of cemiplimab, pembrolizumab, nivolumab, and RMP1-14.

7. The method of claim 5, wherein the anti-PD-L1 antibody is selected from the group consisting of atezolizumab, avelumab, and durvalumab.

8. The method of claim 5, wherein the colorectal cancer is a microsatellite stable-type or microsatellite instable-type colorectal cancer.

9. The method of claim 5, wherein the (E)-N-hydroxy-3-(1-(phenylsulfonyl)-indolin-5-yl)-acrylamide is administered to the subject in the amount of about 2.5-10 mg/kg.

10. The method of claim 5, wherein the anti-PD-1 or anti-PD-L1 antibody is administered to the subject in the amount of about 100 μg/kg-1 mg/kg.

11. The method of claim 5, wherein the subject is a human.

* * * * *